US006979550B1

(12) United States Patent
Rivas et al.

(10) Patent No.: US 6,979,550 B1
(45) Date of Patent: Dec. 27, 2005

(54) METHOD FOR DIAGNOSIS OF, AND DETERMINATION OF SUSCEPTIBILITY TO BOVINE MASTITIS

(76) Inventors: Ariel L. Rivas, 2250 N. Triphammer Rd., Apt. A2, Ithaca, NY (US) 14850; Michael G. Tokman, 3 Cedar La., Itaca, NY (US) 14850; Fred W. Quimby, 504 E. 63rd St., Apt. 24-P, New York, NY (US) 10021

( * ) Notice: Subject to any disclaimer, the term of this patent is extended or adjusted under 35 U.S.C. 154(b) by 80 days.

(21) Appl. No.: 10/235,312

(22) Filed: Sep. 5, 2002

(51) Int. Cl.[7] ......................................... G01N 33/548
(52) U.S. Cl. ..................... 435/7.24; 436/512; 436/513; 435/7.2; 435/4; 435/7.21; 435/7.1; 435/325; 435/326; 435/335
(58) Field of Search .......................... 435/288.7, 287.3, 435/303.3, 808, 288.1, 8, 7.32, 4, 26, 28, 435/7.33, 19, 23, 805, 7.24, 7.5, 7.9, 7.92, 435/961, 174, 7.1, 91.1, 91.2, 7.21, 63, 73, 435/325, 326, 335, 6, 7.2, 962; 436/513, 436/534, 806, 808, 63, 174, 512; 422/56; 530/388.1, 387.1; 600/310; 536/23.1, 24.3

(56) References Cited

U.S. PATENT DOCUMENTS

| 3,917,818 | A | * | 11/1975 | Botes | 424/163.1 |
| 5,168,044 | A | * | 12/1992 | Joyce et al. | 435/7.24 |
| 5,288,642 | A | * | 2/1994 | Turner | 436/8 |
| 6,297,045 | B1 | * | 10/2001 | Takahashi et al. | 435/288.7 |
| 6,787,134 | B1 | * | 9/2004 | Hokase | 424/94.6 |

FOREIGN PATENT DOCUMENTS

WO 00/39578 * 7/2000

OTHER PUBLICATIONS

Rivas, AL et al, Am. J. Vet. Research, Dec. 2001, vol. 62(12), pp. 1840-1851, abstract only.*
Nonnecke, BJ et al, Journal of Diary Science, vol. 72(5), pp. 1313-1327, May 1989, Function and regulation of lymphocyte mediated immune responses relevance to bovine mastitis.*
Daley, MJ et al, Am. J. Vet. Res., vol. 52(3), Mar. 1991, pp. 474-479.*
Dosogne, H et al, Vet. Immunology and immunopathology (Netherlands), Dec. 12, 1997, vol. 60(1-2), pp. 47-59.*
Hebert, A et al, FEMS microbiology, Dec. 1, 2000, vol. 193(1), pp. 57-62.*
Ishikawa, H et al, Journal of Diary Science, Mar. 1983, vol. 66(3), pp. 556-561.*
Smits, E et al, Infection and Immunity, vol. 66(6), pp. 2529-2534, Jun. 1998.*
Soltys, J et al, FASEB Journal, vol. 13(5 part 2), p. A663, Mar. 15, 1999.*
Soltys, J et al, Infection and Immunity, Dec. 1999, vol. 67(12), pp. 6293-6302.*
Sutra, L et al, Journal of Clinical Microbiology, vol. 28(10), Oct. 1990, pp. 2258-2258.*

(Continued)

Primary Examiner—Lynette R. F. Smith
Assistant Examiner—Ginny Allen Portner
(74) Attorney, Agent, or Firm—Hodgson Russ LLP; Ranjana Kadle

(57) ABSTRACT

The present invention discloses a method for detection and prediction of mastitis. The method comprises the steps of determining the values of mastitis indicators and comparing the values with predetermined standards, wherein deviation from the standards provides a measure of mastitis.

7 Claims, 12 Drawing Sheets

OTHER PUBLICATIONS

Vage, DI et al, Animal Genetics, vol. 23(6), 1992, pp. 533-536.*
van Werven, T et al, Veterinary immunology and immunopathology, Apr. 16, 1998, vol. 62(3), pp. 235-244.*
van der Vliet, H et al, Agents and actions, (Switzerland), Jan. 1989, vol. 26(1-2), pp. 211-212.*
Yang, TJ et al, Veterinary immunology and immunopathology, (Netherlands)Apr. 1988, vol. 18(3), pp. 279-285.*
Spencer, R. F. et al., Arch. Opthmolmol, vol. 105, Dec. 1987, p. 1703-1711.*
Ayoub, IA et al, Immunology and Infectious diseases, vol. 6(3/4), pp. 145-150, 1996.*
Burriel, AR et al, APMIS- acta pathologica, microbiologica, et immunologica Sancdinavica (Denmark), Nov. 1997, vol. 105(11), pp. 869-874.*
Daley, MJ et al, Am. J. Vet. Res. vol. 52(3), pp. 474-479. Mar. 1991.*
Kimura, Kayoko et al, J. Dairy Science, vol. 82, pp. 2385-2392.*
Miller, RH et al, Am J. Vet. REs, vol. 54(12), Dec. 1993, pp. 1975-1979.*
Redelman, D et al, Cytometry, vol. 9, pp. 463-468, 1988.*
Rivas, AL et al, The Canadian Journal of Vet. Res., vol. 64, pp. 232-237, 200.*
Saad, AM et al, J. Vet. Med. vol. B 35, pates 654-663, 1988.*
Soltys, J et al, Infection and Immunity, vol. 67(12),pp. 6293-6302, Dec. 1999.*
Van Werven, T et al, Journal of Dairy Science, vol. 80, pates 67-74, 1997.*
Zachos, T et al, Journal of Dairy Science, vol. 59, pp. 461-467, 1992.*
Ayoub, IA, PHD., 1995 Lactation Stage Dependent Profiles of T-Lymphocytes subpopulations & immunoregulator cytokines in mammary secretions.*
Butler, Sara-Del, Flow cytometric characterization of milk leukocytes and the comparison of cell patterns identified in mastitic holstein milk. University of Nevada, 1988.*
Chang, X et al, Veterinary immunology and immunopathology, Jun. 15, 1996, vol. 52(1-2), pp. 37-52.*
Dosogne, H et al, Veterinary immunology and immunopathology, Dec. 1997, vol. 6o (1-2), pp. 47-59.*
Kitchen, *Review of the Progress of Dairy Science: Bovine Mastitis: Milk Compositional Changes and Related Diagnostic Tests,* Journal of Dairy Research (1981) vol. 48, pp. 167-188.
Le Roux, et al., *Proteolysis in Samples of Quarter Milk with Varying Somatic Cell Counts. I. Comparison of Some Indicators of Endogenous Proteolysis in Milk,* Journal of Dairy Science, (1995) vol. 78, No. 6, pp. 1289-1297.
Piccinini, et al., *Study of the Relationship Between Milk Immune Factors and Staphylococcus Aureus Intramammary Infections in Dairy Cows,* Journal of Dairy Research (1999) vol. 66, pp. 501-510.
Redelman, et al., *Identification of Inflammatory Cells in Bovine Milk by Flow Cytometry,* Cytometry, (1988) vol., 9, pp. 463-468.
Schukken, et al., *Genetic Impact on the Risk of Intramammary Infection Following Staphylococcus Aureus Challenge,* Journal of Dairy Science (1994) vol. 77, No. 2, pp. 639-647.
Springer, *Traffic Signals on Endothelium for Lymphocyte Recirculation and Leukocyte Emigration,* Annu. Rev. Physiol. (1995) vol. 57, pp. 827-872.
Wilson, et al., *Association Between Management Practices, Dairy Herd Characteristics, and Somatic Cell Count of Bulk Tank Milk,* J. Am. Vet. Med. Assoc. (May 15, 1997) vol. 210, No. 10, pp. 1499-1502.
Yang, et al., *Lactation Stage-Dependent Changes of Lymphocyte Subpopulations in Mammary Secretions: Inversion of $CD4^+/CD8^+T$ Cell Ratios at Parturition,* American Journal of Reproductive Immunology (1997) vol. 37, pp. 378-383.

* cited by examiner

METHOD FOR DIAGNOSIS OF, AND DETERMINATION OF SUSCEPTIBILITY TO BOVINE MASTITIS

FIELD OF THE INVENTION

This invention relates to the field of animal medicine/animal science. More particularly, this invention provides a method for the diagnosis of, and susceptibility to, mastitis (inflammation of the mammary gland).

DISCUSSION OF RELATED ART

Infectious bovine mastitis is a major health problem of dairy cattle which results in decreased milk production and decreased milk quality. *Staphylococcus aureus* is one of the major bacterial pathogens associated with this disease [1]. Identification of bovine mastitis has historically been based on counting of all cells present in milk (leukocytes and epithelial cells), also known as somatic cell counts (SCC). Counts greater than 500,000/ml are usually associated with bovine mastitis, which results in reduced milk production and reduced shelf-life of dairy products [2,3]. The reduction of bovine mastitis prevalence is a major goal of the dairy industry throughout the world. To achieve this goal, most countries ban from the market milk with SCC>500,000 cells/ml, or charge fees to milk deliveries that approach that figure (Booth J M, National Mastitis Council, 1996 Annual Meeting).

In spite of these policies, it is questionable whether measures based on SCC will ever achieve success in decreasing prevalence of bovine mastitis. While high SCC ($>1\times10^6$ SSC/ml) is regarded to be an accurate indicator of bovine mastitis, both mastitic and healthy cows can yield SCC below that figure. [4] Low SCC may also be associated with milk of poor industrial value [2]. The SCC is a generic number that does not take into account the contribution of different cell types (i.e., lymphocytes, macrophages and polymorphonuclear cells [or PMN]), nor does it measure cell functions. As a result, neither the number nor the function of each of these three cell types is assessed, which prevents accurate diagnosis (determination of present health status) and determination of susceptibility (determination of future health status), as well as evaluation of therapies against mastitis (due to lack of knowledge about their functioning). Furthermore, the SCC does not provide information on the immune status of the individual (i.e., susceptible versus resistant to mastitis). Therefore, there is a need in the dairy industry to develop accurate methods for detection of mastitis that go beyond the SCC paradigm.

The use of differential cell counts in the diagnosis of mastitis has been proposed for two decades [5]. Manual milk cytology is the standard technique used to determine leukocyte differential counts. However, the time-consuming nature of, and expertise required by cytologic evaluations of milk leukocytes may be an impediment for current efforts toward improved diagnosis of bovine mastitis [6]. Cytology only allows a relatively low number of cells to be counted per sample. This feature results in inaccurate counts when specimens with low cell concentrations are assessed [7]. In addition, conventional cytology methods do not differentiate between viable and non-viable cells, nor assess cell function. Assessment of viable cells is relevant when composite leukocyte samples (i.e., containing lymphocytes, PMN and mononuclear cells) are assessed. Cell viability is especially important when milk cells are assessed, since viability of milk leukocytes has been reported to be 20–30% lower than that of peripheral blood [8]. Since inflammatory PMN have a mean-life of a few hours [9], lack of determination of PMN viability may prevent the diagnosis of inflammatory status (i.e., active, with high cell viability; or inactive, with high percentage of apoptotic/necrotic cells). Accordingly, there is a need in the field of dairy industry to develop new approaches to detect the presence of, and susceptibility to mastitis.

SUMMARY OF THE INVENTION

The present invention provides a method for diagnosis of mastitis in a cow. A method is also provided for identifying the stage of mastitis. The method is based on the presence of one or more mastitis biomarkers provided herein. The biomarkers correlate with the presence or absence of mastitis and the stage of mastitis. These procedures and biomarkers can quantify each leukocyte type (lymphocyte, macrophage, polymorphonuclear cell) and assess cell functions (cell activation/cell migration, antigen recognition/antigen binding (immune responsiveness), and phagocytosis), by assessing relationships of various cell types in blood and/or milk, antigen density index of leukocyte cell surface markers and/or percentage of leukocytes identified by these markers, and phagocytic ability of cell sub-populations.

The method of the present invention comprises procedures for identification of each cell type, measurement of the biomarkers described herein, and comparison of the measurements to a standard to identify mastitis stage, wherein deviation from the standard and the extent of deviation is an indication of the presence or absence of mastitis and of the stage of mastitis, and the confidence intervals within which a diagnosis (mastitis/no mastitis) and/or susceptibility to disease, can be made.

In one embodiment, the size and density that identify lymphocytes, monocytes/macrophages and polymorphonuclear (PMN) cells in blood and milk are determined first so that their number can be quantified. Then, the ratio between phagocyte (macrophage and polymorphonuclear cell or PMN) percentage and lymphocyte percentage, and the ratio between the PMN percentage and macrophage percentage is calculated and compared to a pre-determined standard to indicate the presence or absence, and the stage of mastitis (with determination of the likelihood of confidence interval of these events).

In another embodiment, the cell function being evaluated is the ability to start an immune response and the indicator is the antigen density index of cell surface markers (i.e., CD2, CD3) on lymphocytes. The magnitude of these cell surface markers is determined in relation to a certain threshold (greater than or less than) to detect the presence or absence, and the stage of mastitis.

In another embodiment, the cell function being evaluated is cell activation or cell migration. This is determined by measuring the CD3 or CD11b antigen density index on lymphocytes and macrophages. The magnitude of these cell surface markers is determined in relation to a certain threshold (greater than or less than) to detect or predict the presence or absence, and the stage of mastitis.

In another embodiment, the cell function being assessed is the ability of macrophages or PMN to phagocytose. This is determined by measuring an indicator (fluorescent microspheres) which identifies macrophage or PMN sub-populations of different phagocytic ability.

The present invention also provides a method for identifying biomarkers useful for predicting mastitis or lack of mastitis (determination of future health status). The method comprises measuring the magnitude of various markers of leukocytes in blood and/or milk (such as CD2 and CD3—which are constitutive or innate) and are associated with ability to resist mastitis. Thus, measurement of the magnitude of these constitutive markers (i.e., regardless of present health status) can result in prediction of susceptibility for contracting mastitis (future health status).

DETAILED DESCRIPTION OF THE INVENTION

Definitions

Figure 1:
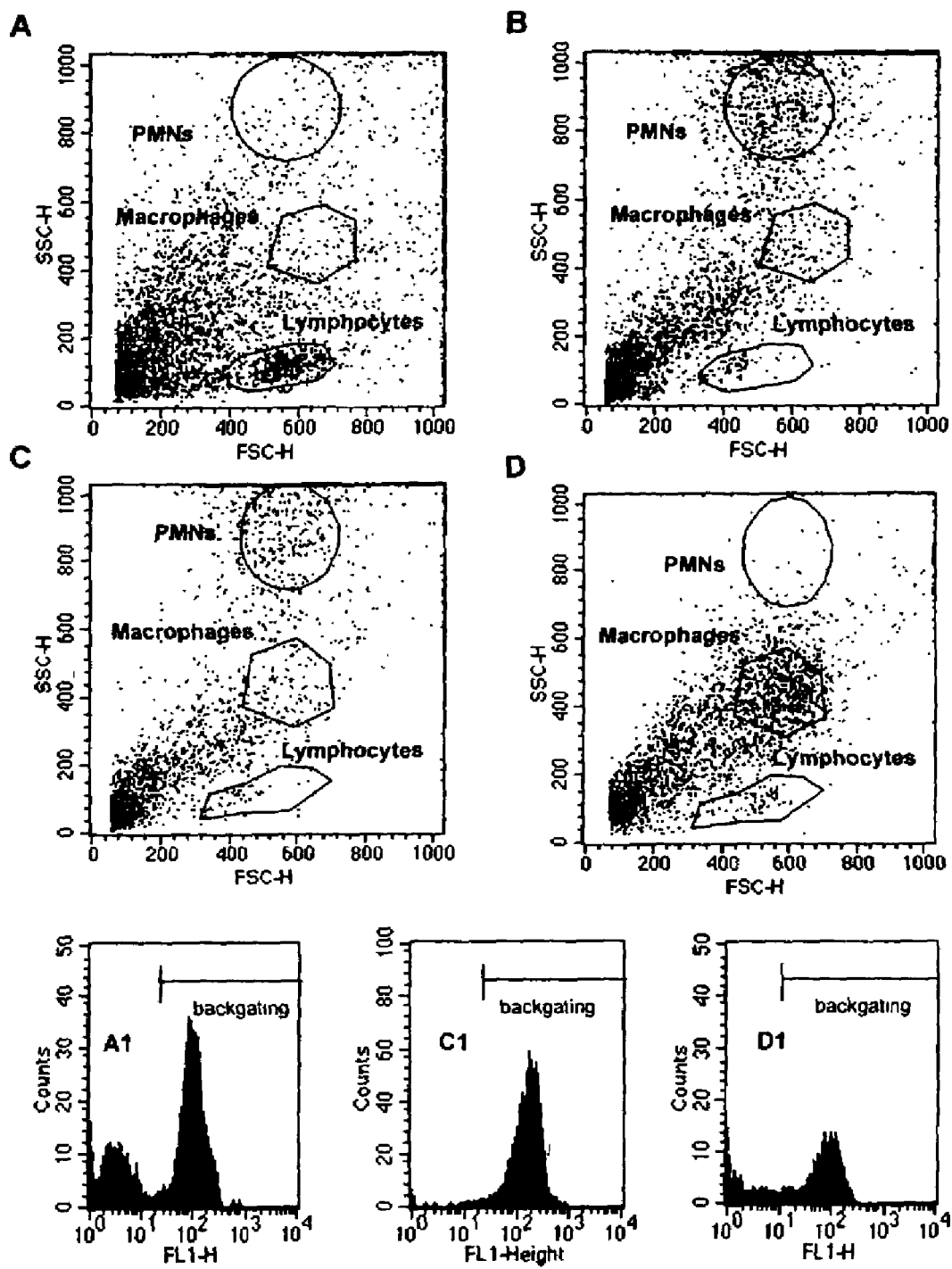
FIG. 1 shows a representative example of scatter light-based quantitation of milk leukocytes. Light reflected as a function of cell size (forward scatter, or FSC-h) and cell density or granularity (side scatter, or SCC-H). A: pre-inoculation. B: 1 day post-inoculation (dpi). C: 4–8 dpi. D: 9–4 dpi. A1: CD3+ fluorescence of sample A (lymphocytes). C1: CD11b fluorescence of sample C (PMN). D1: CD11b fluorescence of sample D (macrophages). Note that seemingly empty bitmaps may include a lower cell density (each dot represents 100 cells).

The term "Differential leukocyte count" as used herein means the relationship of lymphocytes, macrophages and polymorphonuclear cells (PMN) with respect to each other.

The term "Antigen density index" as used herein means the ratio of fluorescence intensity from binding of antibodies to a particular antigen to the fluorescence intensity from the binding of non-specific antibodies.

The term "Lymphocyte antigen density index" as used herein means the ratio of fluorescence intensity from binding of antibodies to CD2+ or CD3+ cell surface antigens to the fluorescence intensity of a non-specific antibody in lymphocytes.

The term "Macrophage (or lymphocyte) cell activation index" as used herein means the antigen density index for CD11 on macrophages (or CD3 on lymphocytes).

The phagocytic ability of phagocytes (macrophages and PMN) can be measured by various methods. One way is to measure the number of fluorescent beads engulfed (phagocytised) by phagocytes and to classify the phagocytic ability according to the number of engulfed fluorescent beads per cell type (macrophage or PMN), cell type population and sub-population. Two major cell populations can be described in both macrophages and PMN based on discontinuities of fluorescence intensity shown after phagocytes engulf fluorescent beads ("low fluorescence intensity" and "high fluorescence intensity"). The term "low fluorescence intensity" (LFI) as used herein means the major population of milk macrophages and PMN which are identified by the fluorescence exhibited by those cells after exposure to fluorescent beads, which is of greater intensity than that of the background (lymphocytes showing <5% cells attached to fluorescent beads), but less intensity than that of the second cell population ("high fluorescence intensity" or HFI).

The term "phagocytosis index"(i.e., macrophage HFI/LFI index) as used herein means the ratio of HFI macrophages over LFI macrophages.

The present invention addresses the problems or deficiencies of SCC and manual cytology (for determination of leukocyte differential counts) Based on measurement of the light reflected by leukocytes as recorded by two mirrors located in the same direction and at a 90-degree angle from the source of light (scatter light), each leukocyte type can be identified and counted, with advantage in terms of time and accuracy over that of SCC and manual cytology. This invention demonstrates that it can quantify leukocyte types with similar or greater accuracy than manual cytology and SCC.

In addition, this invention provides assessment of several leukocyte functions associated with mastitis, information not provided by either SCC or cytology. Three central cell functions are: a) immune responsiveness (the ability to rapidly and efficiently mount an immune response once leukocytes encounter a pathogenic microorganism), b) cell activation/cell migration (the ability to mobilize cell mechanisms such that cells can physically move toward the site of infection and put into operation other mechanisms that eventually would destroy the invading microorganisms), and phagocytosis (the ability of macrophages and PMN to actually engulf and kill microorganisms). These functions are mediated by molecules expressed on the surface of leukocytes, herein described as cell surface markers or biomarkers. They include CD2, CD3, and CD11b. In addition, the use of fluorescent microspheres (beads) can mark the phagocytic ability of phagocyte sub-populations.

The present invention provides a method for the diagnosis of mastitis and for identifying the stage of mastitis. The method comprises procedures for identifying and quantifying cell types, populations and sub-populations within each cell type; and for analyzing the magnitude of the expression of the biomarkers as described herein. The indicators of mastitis are selected from the group consisting of the relationships of various cell types in blood and milk, antigen density index of leukocyte markers, and phagocytic ability of milk phagocytes.

The method of the present invention can be used to detect the presence of, and the stage of mastitis as a substitute for the currently used method of SCC. Further, the present invention can also be used for animal selection practices (i.e., identification of animals resistant to contract mastitis and/or culling of animals susceptible to this disease).

In addition, the algorithms generated from the present invention can be used as the gold standard of therapeutic product evaluation (i.e., evaluation of reagents and therapeutic products seeking approval for agricultural use, which currently are approved without knowledge of their functioning since no methods for evaluation of cell function are available).

The present invention is illustrated by the examples presented below which are not intended to be restrictive in any way.

EXAMPLE 1

Scatter Light-Based Differential Cell Count

Materials and Methods

Animals. Six first-lactation, non-periparturient heifers from Cornell University herds were used. Criteria for use included: 1) no previous history of mastitis; 2) at least three consecutive tests showing no bacterial growth of specific pathogens in milk cultures; and 3) no individual mammary gland quarter somatic cell count (SCC) greater than 200,000/ml and an average of three consecutive measurements less than 100,000 SCC/ml. Animals were fed and milked according to federal and university regulations and housed in AAALAC-accredited facilities. The results of each cow's four tests are reported: the last test before bacterial challenge was conducted (pre-inoculation or pre-infection), and those obtained at one day post-inoculation (dpi), 4–8, and 9–14 dpi.

Experimental challenge, bacterial, and somatic cell counts (SCC). *S. aureus* ribotype 116-232-S3 was cultured in sterile Todd-Hewitt broth (Becton-Dickinson, Franklin Lanes, N.J.) at 37° C. until exponential growth phase was reached, colony-forming units (CFU) were counted and diluted at 200 CFU/ml in the same medium and kept at 4° C. until infused. This strain had been isolated from mastitic cows on a commercial New York dairy farm [10]. After the morning milking, 200 CFU were infused in the right front and left hind mammary gland quarters. The inoculum concentration and viability were assessed before the challenge, as well as immediately after (by culturing the unused inoculum of the same syringe used for the challenge). All milk samples were cultured onto blood agar (100 μl per sample), incubated at 37° C. and CFU were counted after 24 hr. Identification of S. aureus strain was performed on stock and post-challenge milk samples by automated ribotyping as described. All S. aureus isolates recovered from milk of inoculated cows were ribotype 116-232-S3 (data not shown). The milk SCC was determined with a cell counter at the North East Dairy Herd Improvement Association (Ithaca, N.Y.).

Milk leukocyte isolation. A modified version of the protocol described by Schmaltz et al. was used [11]. After disinfection of infused quarters, at least 2 liters of milk (one from each inoculated quarter) were obtained during middle milking in a disinfected milker, transferred to sterile 1-liter bottles containing 10 ml (100×) of antibiotic-antimycotic (catalog 15240-039) and 12.5 ug/ml gentamicin (catalog 15710-015), and transported at 4° C. Milk was diluted in an equal volume of PAE buffer (PBS and 10% acid citrate dextrose and 20 mM EDTA) and centrifuiged 40 minutes at 350 g, 15° C. The supernatant and fat layer were poured off, and the cell pellet was washed three times in PAE. The cell pellet was resuspended in 30 ml of Hanks' Balanced Salt Solution (HBSS), layered on Percoll and centrifuged for 30 minutes at 800 g, 15° C. Leukocytes were then collected, washed three times in 10% fetal bovine serum (FBS)-HBSS and resuspended in 5 ml of complete media. Complete media was RPMI containing 10% FBS and 5% of a tissue culture cocktail containing 0.1 mM non-essential amino acids, 2 mM L-Glutamine, 1 mM sodium pyruvate, 10 mM Hepes buffer and 1× antibiotic-antimycotic. Cell viability was assessed after exposure to trypan blue. Total milk leukocyte counts/ml were calculated based on viable cells.

Cytologic procedures. Milk leukocytes isolated as described above, were collected on slides by cytocentrifugation (10 minutes at 1,200 rpm). Slides were stained with a modified Wright's stain on an automated slide stainer by standard procedures.

Immunophenotyping of leukocyte cell surface markers. Monoclonal antibodies against bovine CD3 and CD11b (both IgG1 isotype; VMRD Inc., Pullman, Wash.) were used. Negative control antibody was of the mouse IgG1 isotype (catalog 08-6599, Zymed, South San Francisco, Calif.). Three million leukocytes were incubated in first wash buffer which contained 2% rabbit serum diluted in pH 7.2 PAE buffer (PBS with 0.1% NaN3, 10% citrate, 10 mM EDTA) and centrifuged for 10 minutes at 350 g. One million cells were then transferred to 12×75 mm polypropylene tubes and resuspended in 50 μl of 10% rabbit serum in PAE. After 10 minutes on ice, 50 μl of the appropriate antibody were added, and incubated for 30 minutes on ice. Cells were washed three times and then incubated with the secondary antibody (100 μl, optimal dilution, FITC-conjugated rabbit anti mouse IgG [H&L chains] in 10% rabbit serum in PAE). Cells were then washed four times, fixed in 500 μl of 2% formaldehyde PBS-azide, and kept in darkness at 4° C. until analyzed by flow cytometry. Cells were processed and fixed within 12 hours of being collected.

Scatter light (flow cytometry) procedures. Cell types were assessed by flow cytometry based on forward and side scatter parameters and confirmation of cell types was based on backgating of CD3+ (T cells) or CD3 cells (monocytes/macrophages, B-cells and PMN) as described [12]. At least 40,000 cells were acquired per test, in order to obtain enough cells of the cell type least represented in each sample. Data were acquired and statistically analyzed with standard software.

Statistical analysis. Six indicators of inflammatory responses were collected or generated from milk leukocyte data: 1) the lymphocyte percentage, 2) the polymorphonuclear cell (PMN) percentage, 3) the macrophage percentage, 4) the Pmn/lymphocyte percent ratio (Pmn/L), 5) the PMN/macrophage percent ratio (Pmn/M), and 6) the phagocyte (PMN and macrophage)/lymphocyte percent ratio (P/L). Results were expressed as medians and analyzed by the Mann-Whitney test. Analysis of medians, correlation analysis and confidence intervals were analyzed with a statistical software. Values of $P \leq 0.05$ were considered significant.

Results

Manual cytology-scatter light (flow cytometry) comparisons of leukocyte percents and counts. Milk leukocyte viability ranged between 60 and 75% (data not shown). At pre-inoculation, lymphocytes were identified by cytology to predominate in the milk leukocyte population (median: 69.20%, with individual values ranging from 56.5, lower limit; and 77.5, upper limit, 95% confidence interval or C.I.). At 1 dpi, the lymphocyte percent decreased more than twofold (median: 30.2%, lower limit: 18.7, upper limit: 37.3, 95% C.I., P<0.01). At later observations, the lymphocyte percent increased (median: 39.2 and 46.0, at 4–8 dpi and at 9–14 dpi, respectively). A greater percent was observed at 9–14 dpi that at 1 dpi observations (P=0.03). Multiplied by the total leukocyte count/ml, these values represented a median of 3.95, 3.34, 7.99 and 5.83 million lymphocytes per ml at pre-inoculation, 1, 4–8 and 9–14 dpi, respectively. Therefore, there was a transient reduction in the median count of milk lymphocytes 24 hours after challenge, followed by a 2-fold increase at 4–8 dpi (Table 1).

TABLE 1

Total milk leukocyte count, leukocyte percentages, and leukocyte counts/ml
(as determined by conventional cytology)
before and after experimental S. aureus infection.

| | Variable | | | | | | |
|---|---|---|---|---|---|---|---|
| Cow, time | Milk cells* | Lymp (%)† | PMN (%)† | MO (%)† | Lymp ($10^6$/ml)‡ | PMN ($10^6$/ml)‡ | MO ($10^6$/ml)‡ |
| A, pre-i.§ | 6.0 | 79.5 | 6.0 | 15.0 | 4.77 | 0.36 | 0.90 |
| 1 dpi‖ | 40.0 | 20.5 | 60.0 | 19.5 | 8.20 | 24.00 | 7.80 |
| 4–8 dpi | 10.5 | 48.5 | 33.5 | 18.0 | 5.09 | 3.51 | 1.89 |
| 9–14 dpi | 11.0 | 50.0 | 21.0 | 29.0 | 5.50 | 2.31 | 3.19 |
| B, pre-i. | 6.6 | 67.0 | 6.5 | 26.5 | 4.42 | 0.42 | 1.74 |
| 1 dpi | 12.8 | 35.5 | 36.5 | 28.0 | 4.54 | 4.67 | 3.58 |
| 4–8 dpi | 19.0 | 42.5 | 19.0 | 38.5 | 8.07 | 3.61 | 7.31 |
| 9–14 dpi | 17.5 | 52.5 | 11.5 | 35.0 | 9.18 | 2.01 | 6.12 |
| C, pre-i. | 3.8 | 54.0 | 6.5 | 39.5 | 2.05 | 0.24 | 1.50 |
| 1 dpi | 6.8 | 31.5 | 34.5 | 34.0 | 2.14 | 2.34 | 2.31 |
| 4–8 dpi | 22.0 | 36.0 | 26.5 | 37.5 | 7.92 | 5.83 | 8.25 |
| 9–14 dpi | 22.0 | 42.0 | 30.0 | 28.0 | 9.24 | 6.60 | 6.16 |
| D, pre-i. | 7.5 | 56.5 | 31.0 | 12.5 | 4.23 | 2.32 | 0.93 |
| 1 dpi | 4.0 | 37.0 | 42.5 | 20.0 | 1.48 | 1.70 | 0.80 |
| 4–8 dpi | 27.0 | 24.0 | 62.0 | 14.0 | 6.48 | 16.74 | 3.78 |
| 9–14 dpi | 16.0 | 38.5 | 35.5 | 25.0 | 6.16 | 5.68 | 4.00 |

TABLE 1-continued

Total milk leukocyte count, leukocyte percentages, and leukocyte counts/ml (as determined by conventional cytology) before and after experimental *S. aureus* infection.

| Cow, time | Milk cells* | Lymp (%)† | PMN (%)† | MO (%)† | Lymp ($10^6$/ml)‡ | PMN ($10^6$/ml)‡ | MO ($10^6$/ml)‡ |
|---|---|---|---|---|---|---|---|
| E, pre-i. | 3.0 | 71.5 | 7.5 | 21.0 | 2.14 | 0.22 | 0.63 |
| 1 dpi | 5.7 | 14.5 | 73.5 | 12.0 | 0.82 | 4.18 | 0.68 |
| 4–8 dpi | 42.0 | 24.0 | 70.5 | 5.5 | 10.08 | 29.61 | 2.31 |
| 9–14 dpi | 28.4 | 19.0 | 71.5 | 9.5 | 5.39 | 20.30 | 2.69 |
| F, pre-i. | 5.0 | 73.5 | 3.0 | 24.0 | 3.67 | 0.15 | 1.20 |
| 1 dpi | 74.0 | 29.0 | 61.5 | 9.5 | 21.46 | 45.51 | 7.03 |
| 4–8 dpi | 20.0 | 51.0 | 22.5 | 26.5 | 10.20 | 4.50 | 5.30 |
| 9–14 dpi | 7.5 | 53.0 | 20.0 | 27.0 | 3.97 | 1.50 | 2.02 |

*Total leukocyte count ($1 \times 10^6$/ml)
†Lymphocyte (Lymp), Polymorphonuclear cell (PMN), and macrophage (MO) percentage
‡Lymp/PMN/MO counts/ml
§pre-inoculation
∥day(s) post-inoculation (post-experimental infection)

In agreement with cytologic findings, flow cytometry data indicated that the median lymphocyte percentage was highest at pre-inoculation (median: 72.7%), and decreased significantly 24 hours after challenge (median: 11.6%, P<0.003). Later, it increased (median: 23.2% at 4–8 dpi, and 31.6% at 9–14 dpi). At the late inflammatory phase (9–14 dpi), the lymphocyte percentage was significantly higher than at 1 dpi (P<0.04). Multiplied by the total leukocyte count/mil, these values represented a median of 3.99, 3.32, 4.35 and 4.43 million lymphocytes per ml at pre-inoculation, 1, 4–8 and 9–14 dpi, respectively (Table 2).

FIG. 1 describe the settings for identification of each cell type (lymphocyte, macrophage, PMN) were determined by scatter light, based on cell size (forward scatter) and cell density (side scatter), and confirmed by fluorescent markers specific of lymphocytes (CD3+, CD11b−) and phagocytes (CD3−, CD11b+).

TABLE 2

Total milk leukocyte count, leukocyte percentages, and leukocyte counts/ml (as determined by flow cytometry) before and after *S. aureus* inoculation.

| Cow, time | Milk Cells* | Lymp (%)† | PMN (%)† | MO (%)† | Lymp ($10^6$/ml)‡ | PMN ($10^6$/ml)‡ | MO ($10^6$/ml)‡ |
|---|---|---|---|---|---|---|---|
| A, pre-i.§ | 6.0 | 79.5 | 14.2 | 6.3 | 4.77 | 0.85 | 0.37 |
| 1 dpi∥ | 40.0 | 9.8 | 68.8 | 21.4 | 3.92 | 27.52 | 8.56 |
| 4–8 dpi | 10.5 | 23.3 | 4.6 | 72.0 | 2.44 | 0.48 | 7.56 |
| 9–14 dpi | 11.0 | 10.8 | 5.4 | 83.8 | 1.19 | 0.59 | 9.21 |
| B, pre-i. | 6.6 | 81.6 | 15.0 | 3.4 | 5.38 | 0.99 | 0.22 |
| 1 dpi | 12.8 | 28.8 | 60.0 | 11.2 | 3.68 | 7.68 | 1.43 |
| 4–8 dpi | 19.0 | 52.2 | 29.4 | 18.4 | 9.91 | 5.58 | 3.49 |
| 9–14 dpi | 17.5 | 53.2 | 24.4 | 22.4 | 9.31 | 4.27 | 3.92 |
| C, pre-i. | 3.8 | 68.8 | 11.5 | 19.7 | 2.61 | 0.43 | 0.74 |
| 1 dpi | 6.8 | 43.6 | 37.1 | 19.3 | 2.96 | 2.52 | 1.31 |
| 4–8 dpi | 22.0 | 8.0 | 73.0 | 19.0 | 1.76 | 16.06 | 4.18 |
| 9–14 dpi | 22.0 | 40.6 | 34.9 | 24.4 | 8.93 | 7.67 | 5.37 |
| D, pre-i. | 7.5 | 63.0 | 36.2 | 0.8 | 4.72 | 2.71 | 0.06 |
| 1 dpi | 4.0 | 13.4 | 75.4 | 11.2 | 0.53 | 3.01 | 0.44 |
| 4–8 dpi | 27.0 | 23.2 | 62.9 | 13.9 | 6.26 | 16.98 | 3.75 |
| 9–14 dpi | 16.0 | 22.6 | 34.2 | 43.2 | 3.61 | 5.47 | 6.91 |

TABLE 2-continued

Total milk leukocyte count, leukocyte percentages, and leukocyte counts/ml (as determined by flow cytometry) before and after *S. aureus* inoculation.

| Cow, time | Milk Cells* | Lymp (%)† | PMN (%)† | MO (%)† | Lymp ($10^6$/ml)‡ | PMN ($10^6$/ml)‡ | MO ($10^6$/ml)‡ |
|---|---|---|---|---|---|---|---|
| E, pre-i. | 3.0 | 76.7 | 16.0 | 7.3 | 2.30 | 0.48 | 0.21 |
| 1 dpi | 5.7 | 4.4 | 85.6 | 10.0 | 0.25 | 4.87 | 0.57 |
| 4–8 dpi | 42.0 | 5.1 | 85.0 | 9.9 | 2.14 | 35.70 | 4.15 |
| 9–14 dpi | 28.4 | 9.7 | 75.5 | 14.8 | 2.75 | 21.44 | 4.20 |
| F, pre-i. | 5.0 | 65.1 | 15.2 | 19.7 | 3.25 | 0.76 | 0.98 |
| 1 dpi | 74.0 | 9.7 | 41.9 | 48.4 | 7.17 | 31.00 | 35.81 |
| 4–8 dpi | 20.0 | 38.1 | 18.7 | 43.2 | 7.62 | 3.74 | 8.64 |
| 9–14 dpi | 7.5 | 69.8 | 12.8 | 17.4 | 5.23 | 0.96 | 1.30 |

*Total leukocyte count ($1 \times 10^6$/ml)
†Lymphocyte (Lymp), Polymorphonuclear cell (PMN), and macrophage (MO) percentage
‡Lymp/PMN/MO counts/ml
§pre-inoculation
∥day(s) post-inoculation The PMN percentage was shown by cytology to be greater at the early rather than at the late inflammatory phase. At 9–14 dpi there was a 2-fold reduction compared to the 1 dpi PMN percent (P=0.03, Table 1). There was no statistical difference in the percent of macrophages among post-inoculation observations.

In agreement with cytologic findings, flow cytometric data indicated that the PMN percent showed a 2-fold reduction between the early and the late (9–14 dpi) observations (P<0.02). A greater percent of macrophages was observed at 9–14 dpi than at 1 dpi, which approached statistical significance (P=0.08, Table 2).

Manual cytology-scatter light (flow cytometry) comparisons of leukocyte indices. Decreased PMN percents and increased lymphocyte percents were observed by cytology at the late inflammatory phase. These changes resulted in a PMN/lymphocyte percent ratio significantly lower at 9–14 dpi than at 1 dpi (P=0.02). Similarly, a significantly lower PMN/lymphocyte percent ratio was observed by flow cytometry at 9–14 dpi (median: 0.68) than at 1 dpi (median: 4.97, P<0.03, Table 3).

TABLE 3

Relationship between PMN/lymphocyte percents, Phagocyte (PMN and macrophage)/ Lymphocyte percent index (P/L), PMN/Macrophage percent index (P/M) (as determined by conventional cytology and flow cytometry), SCC, and bacterial counts before and after *S. aureus* inoculation.

| Cow, time | Cyt PMN/L* | SL PMN/L* | Cyt. P/L† | SL P/L† | Cyt. P/M‡ | SL P/M‡ | SCC§ | CFU∥ |
|---|---|---|---|---|---|---|---|---|
| A, pre-i.¶ | 0.07 | 0.17 | 0.26 | 0.25 | * | * | 21 | 0 |
| 1 dpi# | 2.92 | 7.02 | 3.88 | 9.20 | 3.08 | 3.21 | 403 | 0 |
| 4–8 dpi | 0.69 | 0.19 | 1.06 | 3.28 | 1.86 | 0.06 | 420 | 0 |
| 9–14 dpi | 0.42 | 0.50 | 1.00 | 8.25 | 0.72 | 0.06 | 64 | 0 |
| B, pre-i. | 0.09 | 0.18 | 0.49 | 0.22 | * | * | 42 | 0 |
| 1 dpi | 1.02 | 2.08 | 1.82 | 2.47 | 1.30 | 5.35 | 370 | 0 |
| 4–8 dpi | 0.44 | 0.56 | 1.35 | 0.91 | 0.49 | 1.59 | 135 | 0 |

TABLE 3-continued

Relationship between PMN/lymphocyte percents,
Phagocyte (PMN and macrophage)/
Lymphocyte percent index (P/L),
PMN/Macrophage percent index (P/M)
(as determined by conventional cytology and flow cytometry),
SCC, and bacterial counts before and after *S. aureus* inoculation.

| Cow, time | Cyt PMN/L* | SL PMN/L* | Cyt. P/L† | SL P/L† | Cyt. P/M‡ | SL P/M‡ | SCC§ | CFU‖ |
|---|---|---|---|---|---|---|---|---|
| 9–14 dpi | 0.21 | 0.45 | 0.88 | 0.87 | 0.33 | 1.08 | 55 | 0 |
| C, pre-i. | 0.12 | 0.16 | 0.85 | 0.45 | * | * | 47 | 0 |
| 1 dpi | 1.09 | 0.85 | 2.17 | 1.29 | 1.01 | 1.92 | 23 | 1575 |
| 4–8 dpi | 0.73 | 9.12 | 1.78 | 11.50 | 0.71 | 3.84 | 6479 | 16675 |
| 9–14 dpi | 0.71 | 0.85 | 1.81 | 1.46 | 1.07 | 1.43 | 1453 | 50430 |
| D, pre-i. | 0.54 | 0.57 | 0.77 | 0.58 | * | * | 15 | 0 |
| 1 dpi | 1.14 | 5.62 | 1.69 | 6.46 | 2.12 | 6.73 | 36 | 2 |
| 4–8 dpi | 2.58 | 2.71 | 3.17 | 3.31 | 4.43 | 4.52 | 45 | 2685 |
| 9–14 dpi | 0.92 | 1.51 | 1.57 | 3.42 | 1.42 | 0.79 | 2267 | 1405 |
| E, pre-i. | 0.10 | 0.20 | 0.40 | 0.30 | * | * | 94 | 0 |
| 1 dpi | 5.06 | 19.45 | 5.90 | 21.72 | 6.12 | 8.56 | 174 | 165 |
| 4–8 dpi | 2.93 | 16.66 | 3.17 | 18.60 | 12.82 | 8.58 | 3266 | 3135 |
| 9–14 dpi | 3.76 | 7.78 | 4.26 | 9.30 | 7.53 | 5.10 | 5104 | 5435 |
| F, pre-i. | 0.04 | 0.23 | 0.37 | 0.53 | * | * | 17 | 0 |
| 1 dpi | 2.12 | 4.31 | 2.45 | 9.30 | 6.47 | 0.86 | 1904 | 1 |
| 4–8 dpi | 0.44 | 0.49 | 0.85 | 0.54 | 0.85 | 0.43 | 166 | 0 |
| 9–14 dpi | 0.37 | 0.18 | 0.89 | 0.43 | 0.74 | 0.73 | 36 | 10 |

*Cytology-based (Cyt) or scatter light-based (SL) PMN/lymphocyte percent index
†Cytology-based (Cyt) or scatter light-based (SL) phagocyte (PMN and macrophage)/lymphocyte percent index (P/L)
‡Cytology-based (Cyt) or scatter light-based (SL) PMN/macrophage percent index (P/M)
§Somatic cell count ($1 \times 10^3$/ml)
‖*S. aureus* colony-forming units/ml recovered in milk cultures (mean of 2 or 4 cultured plates/sample)
¶pre-inoculation
day(s) post-inoculation The highest PMN/macrophage index (PMN/M) was observed by cytology at 1 dpi (median: 2.60). Although this index decreased later (1.46 at 4–8 dpi, and 1.25 at 9–14 dpi), no statistically significant differences were found among post-challenge observations. The PMN/M ratio was also highest at 1 dpi as determined by flow cytometry (median: 4.29) and lower at 9–14 dpi (median: 0.94). In contrast to conventional (manual) cytologic findings, flow cytometric values were statistically significantly lower at the late inflammatory phase (P<0.03, Table 3).

The median pre-inoculation index of phagocyte/lymphocyte percent ratio (P/L) was 0.45 (as determined by cytology) and increased at 1 dpi (P<0.01). At later observations, the median of this index was 1.56 (4–8 dpi) and 1.19 (9–14 dpi), showing a significantly lower index at 9–14 dpi than at 1 dpi (P<0.04). Similarly, flow cytometry indicated that the Phago/L index was 20-fold greater at 1 dpi than before challenge (median s: 7.83 vs. 0.38, respectively, P<0.003, Table 3).

These findings revealed two differences between these techniques. A significantly greater pre-inoculation macrophage percent was indicated by manual cytology than by flow cytometric data (P<0.02). Cytology also displayed greater 1 dpi lymphocyte percent than flow cytometry, which approached statistical significance (P=0.06).

Opposite relationships were observed between phagocyte percentages both by manual cytology and flow cytometry. The correlation coefficients between postinoculation PMN percents vs. post-inoculation macrophage percents were greater than −0.66 (P<0.001).

Figure 2:
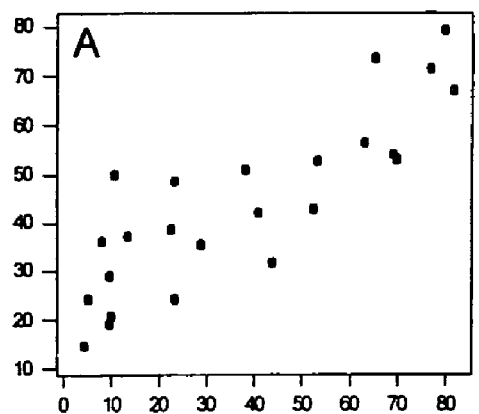
FIG. 2 shows the correlations between flow cytometric and cytologic results. A: lymphocyte percents (r=0.85). B: PMN percents (r=0.82). C: phagocyte (PMN and macrophage)/lymphocyte percent ratio (r=0.80). D: PMN/lymphocyte percent ratio (r=0.84). X axis: flow cytometry. Y axis: cytology. All correlations were statistically significant ($P<0.01$).
Figure 2:
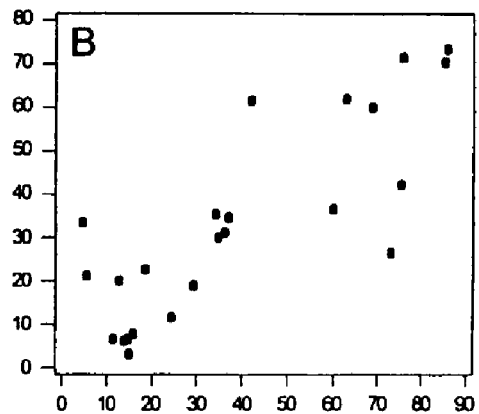
Figure 2:
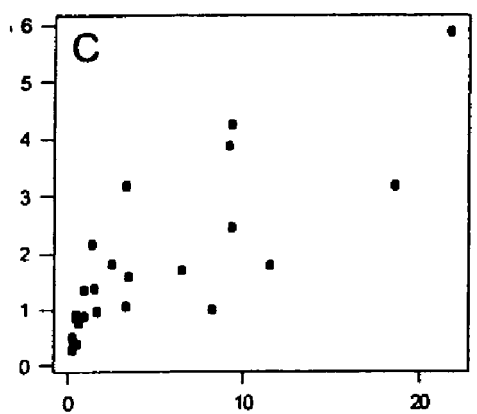
Figure 2:
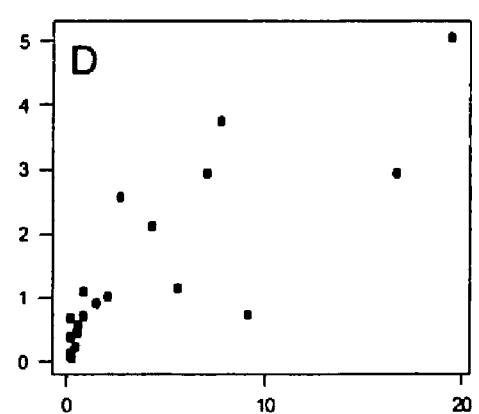

Positive correlations were observed between cytology and flow cytometry in terms of lymphocyte percent (r=0.85), PMN percent (r=0.82), Phago/L index (r=0.80), PMN/L (r=0.84) and PMN/M percent (r=0.61). All of these correlations were highly statistically significant (P≦0.01, FIG. 2).

Comparisons between SCC and scatter light (flow cytometry). All cows had increased SCC after inoculation. In contrast, post-inoculation bacterial growth in milk cultures was not observed in every cow (Table 3). Yet, all cows presented evidence of inflammatory changes after inoculation (i.e., increased percentage of phagocytes and greater milk leukocyte count/ml, Table 1).

SCC and bacteriology were not significantly associated. While SCC showed a statistically significant correlation with the phagocyte/lymphocyte index, the correlation coefficient was marginal (r=0.48, P<0.02). Similarly, a significant but low correlation coefficient was found between SCC and the flow cytometric-based PMN percent (r=0.51, P=0.01). No association was observed between SCC and flow cytometric-based macrophage percents.

The sensitivity and specificity of SCC for diagnosing inflammation were compared to those of flow cytometry. SCC showed a similar sensitivity than flow cytometry (92% vs. 100%). In contrast, the specificity of SCC was markedly lower than that of flow cytometry: only 45% of the truly negative cases were so identified by SCC while the specificity of flow cytometry was 83% (Table 4).

TABLE 4

Sensitivity and specificity of SCC and the scatter light-determined phagocyte/lymphocyte percent ratio (P/L).

|  | Positive | Negative | Total |
|---|---|---|---|
| SCC |  |  |  |
| True* | 12 | 5 |  |
| False# | 1 | 6 |  |
| Totals: | 13 | 11 | 24 |
| P/L |  |  |  |
| True | 18 | 5 |  |
| False | 0 | 1 |  |
| Totals: | 18 | 6 | 24 |

*True positive (TP) and true negative (TN) results are defined as:
a): TP: those above the upper limit of pre-inoculation 95% confidence intervals (C.I.) which also show either bacterial growth and/or changes beyond the 95% C.I. of any other pre-inoculation flow cytometry-based indicator (i.e., increased PMN percent, decreased lymphocyte percent);
b) TN: those below the upper limit of pre-inoculation 95% C.I. which also show neither bacterial growth nor changes beyond the 95% C.I. of any other pre-inoculation flow cytometry-based indicator.
False positive (FP) and false negative (FN) results are defined as:
a) FP: those above the upper limit of pre-inoculation 95% C.I. which also show neither bacterial growth nor changes beyond the 95% C.I. of any other pre-inoculation flow cytometry-based indicator;
b) FN: those below the upper limit of pre-inoculation 95% C.I. which also show bacterial growth and/or changes beyond the 95% C.I. of any other pre-inoculation flow cytometry-based indicator.

Identification of inflammatory phases. Neither SCC nor bacteriology distinguished inflammatory phases. For example, similar SCC values were observed in different health conditions. SCC in the order of $1 \times 10^4$ were observed both at pre-inoculation and 1 dpi (i.e., cows 'B''C' and 'D', Table 3). Bacterial counts did not differentiate early from late inflammatory phases in cows showing bacterial recovery.

The scatter light (flow cytometric) indicators developed from the data allowed the identification of, at least, three health conditions: 1) healthy (no inflammation), 2) early inflammation (1–8 days post-infection or dpi), and 3) late (9–14 dpi) inflammation. Based on the confidence intervals generated from these indicators at each sampling period, an algorithm was developed. No inflammation was characterized (95% confidence intervals or C.I.) by: a) the lymphocyte percent (>64.2%), b) the phagocyte (PMN and macrophage)/lymphocyte percent ratio (<0.55), and c) the PMN/lymphocyte percent index (<0.42). The early inflammatory phase (1–8 dpi) was characterized by: a) the PMN percent (>48.2%, 80% C.I.), b) the PMN/lymphocyte index (>4.95, 95% C.I.), c) the PMN/macrophage index (>5.40, 85% C.I.), and d) the phagocyte/lymphocyte index (>0.73 but <8.04, 95% C.I.). The late inflammatory phase (9–14 dpi) was characterized (95% C.I.) by: a) the lymphocyte percent (>43.8% but <60.0%), and b) the PMN percent (<48.1 but >24.3, 80% C.I.). An additional timeframe (the 4–14 dpi inflammatory period) was characterized by the PMN/macrophage index (<2.39, 85% C.I.).

Based on the data presented herein, several indicators of the presence or absence of mastitis can be developed. For example, a lymphocyte percentage can be one indicator. A lymphocyte percentage greater than 52.7 indicates non-inflammation, a lymphocyte percentage greater than 21.4 and less than 52.7 indicates either greater than 4 dpi inflammation or non-inflammation, and a lymphocyte percentage less than 21.4 indicates early inflammation. Another example of an indicator is the ratio of phagocyte percentage and lymphocyte percentage (referred to herein as P/L). A P/L value of less than 0.52 indicates non-inflammation or late inflammation, a P/L value of greater than 0.52 and less than 1.19 indicates inflammation, a P/L value of less than 8.34 indicates inflammation (probably late phase) and a P/L value of greater than 8.34 indicates 1–8 dpi inflammation. A yet another example of an indicator is the phagocyte inflammatory index which is the ratio of the PMN percentage to macrophage percentage (referred to herein as Pmn/M). A Pmn/M value greater than 3.41 indicates 1–8 dpi inflammation and a Pmn/M value of less than 3.0 indicates greater than 9 dpi inflammation. From these examples and from the data presented herein those skilled in the art will recognize that other indicators of the absence or presence of mastitis may be developed. By using more than one indicator, the accuracy of the method will increase.

Those skilled in the art will recognize that based on the teachings provided herein, diagnostic algorithms may be developed for other pathogens and animals.

The validity of flow cytometric findings was supported by use of monoclonal antibodies (i.e., backgating on CD3+ for T lymphocytes; and CD3− and CD11b+ for phagocytes, which also differed in their scatter light values: low size and high granularity, for PMN; and greater size and lower granularity for monocytes/macrophages). While the validity of the phagocyte regions was uncertain in samples of non-inflamed cows (due to their low percentage), in mastitic samples the combination of backgating on fluorescent cells (stained with specific markers, such as CD11b) and scatter light, identified both macrophages and PMN, even in the presence of milk fat (FIG. 1). Statistically significant correlations found between manual cytology and flow cytometry findings in all of the four measures evaluated (FIG. 2), further validated flow cytometry as a diagnostic approach for identification of bovine mastitis. Previous reports have indicated that flow cytometry has similar or higher sensitivity and specificity than cytology.

An algorithm was constructed based on confidence intervals of flow cytometric-constructed indicators obtained at different times. This algorithm, if added to flow cytometry acquisition software, could facilitate the standardization and dissemination of diagnostic services and/or research aimed at prevention of bovine mastitis.

These data indicate that: 1) scatter light-based milk leukocyte differential counting is a valid diagnostic approach, which provides results comparable to those of manual cytology; 2) the ability of SCC to detect truly negative (non-mastitic) samples is poorer than that of scatter light-based leukocyte differential counting; and 3) scatter light-based indices can be used to develop algorithms which may identify three mammary gland health-related conditions (absence of mastitis, early and late mastitis).

EXAMPLE 2

Lymphocyte ability to elicit efficient immune responses

The ability to prevent development of infection (expressed as bacteria found in milk) and inflammation (expressed as high SCC) was assessed in leukocytes obtained and isolated as described in Example 1. Monoclonal antibodies (all IgG1 isotype) against bovine CD3, and CD2 molecules (VMRD Inc., Pullman, Wash., USA; clones: MM1A, and BAQ95A, respectively) were used. Negative control antibody was a IgG1 mouse antibody (catalog 08-6599, Zymed, South San Francisco, Calif., USA). Approximately five million leukocytes were incubated in first wash buffer which contained 2% rabbit serum diluted in pH 7.2 PAE buffer (PBS with 0.1% $NaN_3$, 10% citrate, 10 mM EDTA) and centrifuged for 10 minutes at 350 g. One million cells were then transferred to 12×75 mm polypropylene tubes (one for each primary antibody including isotype control) and resuspended in 50 $\mu$L of 10% rabbit serum in PAE. After 10 minutes on ice, 50 $\mu$L of isotype control or monoclonal antibody were added to each tube and incubated for 30 minutes on ice. Cells were washed three times with first wash buffer and then incubated with 100 $\mu$L of the secondary antibody (optimal dilution, FITC-conjugated rabbit anti mouse IgG [H&L chains] in 10% rabbit serum in PAE). Cells were then washed four times with first wash buffer, fixed in 500 $\mu$L of 2% formaldehyde PBS-azide, and refrigerated until analyzed by flow cytometry (FACS-Calibur, Becton-Dickinson, San Jose, Calif., USA). In all tests, bovine cells were isolated, labeled and fixed within twelve hours of being collected. Fluorescence data were acquired and analyzed with CELLQuest© software (Becton-Dickinson). Gates of each leukocyte type were customized to achieve the lowest percent of non-specific fluorescence and the highest percent of specific fluorescence, as reported before. At least 40,000 cells were acquired per test.

Surface antigen density index (ADI) was defined as the ratio between CD3 or CD2 median fluorescence intensity (MFI) divided by the isotype control's MFI. Student's t and Mann-Whitney statistical tests, correlation coefficients and regression analysis were calculated with a commercial software (Minitab, State College, Pa., USA).

Significantly higher percentages of CD2+ cells were found in milk than in blood, before and after challenge ($P \leq 0.02$). The percent of milk CD2+ cells (before and after challenge) was negatively correlated with SCC (r=−0.53, P≦0.01, Table 5). The percentage of CD3+ cells did not differ between blood and milk before challenge, but it decreased in blood and increased in milk after challenge, reaching statistical significance at 9–14 dpi (P≦0.01).

TABLE 5

Longitudinal CD2 and CD3 expression, somatic cells counts and bacterial counts in response to intramammary *S. aureus* inoculation.

| Time/cow | Blood Percentages | | | Milk Percentages* | | | SCC[a]* | CFU[b]* |
|---|---|---|---|---|---|---|---|---|
| | Ctl | CD3 | CD2 | Ctl | CD3 | CD2 | | |
| Pre-i | | | | | | | | |
| A | 0.8 | 66.7 | 61.6 | 0.4 | 56.1 | 77.9 | 21 | 0 |
| B | 0.3 | 73.4 | 68.0 | 1.3 | 69.5 | 73.0 | 43 | 0 |
| C | 0.5 | 64.9 | 55.2 | 0.7 | 71.8 | 71.9 | 47 | 0 |
| D | 0.6 | 74.0 | 71.3 | 0.1 | 95.0 | 94.5 | 15 | 0 |
| E | 1.1 | 64.2 | 54.4 | 3.0 | 83.6 | 85.6 | 94 | 0 |
| F | 0.1 | 71.6 | 58.8 | 0.1 | 78.2 | 78.7 | 17 | 0 |
| 1 dpi | | | | | | | | |
| A | 0.7 | 86.1 | 79.9 | 7.6 | 90.3 | 89.4 | 403 | 0 |
| B | 0.2 | 76.2 | 73.3 | 1.5 | 90.4 | 89.2 | 370 | 0 |
| C | 0.5 | 62.5 | 53.7 | 0.3 | 72.6 | 77.7 | 23 | 16675 |
| D | 0.4 | 72.5 | 69.7 | 1.1 | 84.4 | 79.9 | 36 | 2685 |
| E | 0.5 | 54.0 | 48.7 | 3.5 | 67.7 | 70.0 | 174 | 3135 |
| F | 0.8 | 62.3 | 48.6 | 2.3 | 67.8 | 67.8 | 1904 | 6360 |
| 4–8 dpi | | | | | | | | |
| A | 1.1 | 76.1 | 74.9 | 5.6 | 75.7 | 75.7 | 420 | 0 |
| B | 0.3 | 69.9 | 70.2 | 0.5 | 90.9 | 91.6 | 135 | 0 |
| C | 0.2 | 67.2 | 58.9 | 0.2 | 73.1 | 65.4 | 6479 | 2685 |
| D | 0.6 | 79.0 | 77.9 | 0.3 | 88.9 | 86.7 | 90 | 1405 |
| E | 0.5 | 61.1 | 54.4 | 0.7 | 66.5 | 59.8 | 3266 | 0 |
| F | 1.4 | 77.1 | 63.7 | 0.1 | 91.6 | 89.9 | 166 | 165 |
| 9–14 dpi | | | | | | | | |
| A | 0.4 | 77.9 | 66.8 | 0.9 | 85.4 | 85.9 | 65 | 0 |
| B | 0.9 | 58.3 | 61.9 | 1.9 | ND | 85.1 | 55 | 0 |
| C | 0.7 | 69.7 | 64.7 | 1.4 | 63.6 | 59.8 | 1453 | 50430 |
| D | 2.5 | 69.6 | 68.5 | 0.9 | 91.5 | 87.1 | 2267 | 1405 |
| E | 0.8 | 54.4 | 43.2 | 0.8 | 88.1 | 72.0 | 5104 | 5435 |
| F | 0.5 | 29.9 | 27.0 | 0.1 | 95.2 | 91.4 | 51 | 5000 |

*Values reported are composite means determined from both inoculated quarters
(A–F) individual animals; Ctl - control antibody; dpi - day(s) post-inoculation; pre-i - pre-inoculation
[a]somatic cell count ($10^3$/mL, composite milk count)
[b]*S. aureus* cfu/mL (composite milk count)

Significant post-inoculation increases were noted at 1 dpi in the milk median fluorescence intensity (antigen density per lymphocyte) of all of these markers (P≦0.01, Table 6).

TABLE 6

Longitudinal CD3 and CD2 antigen density (median fluorescence intensity and index) in response to intramammary *S. aureus* inoculation.

| Time/Cow | Blood MFI | | | Blood ADI | | Milk MFI* | | | Milk ADI* | |
|---|---|---|---|---|---|---|---|---|---|---|
| | Ctl | CD3 | CD2 | CD3 | CD2 | Ctl | CD3 | CD2 | CD 3 | CD2 |
| Pre-i | | | | | | | | | | |
| A | 10 | 86 | 86 | 8.6 | 8.6 | 34 | 18 | 26 | 0.53 | 0.76 |
| B | 18 | 112 | 60 | 6.2 | 3.3 | 21 | 31 | 38 | 1.48 | 1.81 |
| C | 16 | 73 | 73 | 4.6 | 4.6 | 40 | 44 | 49 | 1.10 | 1.22 |
| D | 12 | 99 | 47 | 8.2 | 3.9 | 32 | 78 | 63 | 2.44 | 1.97 |
| E | 20 | 112 | 59 | 5.6 | 2.9 | 28 | 55 | 64 | 1.96 | 2.28 |
| F | 34 | 81 | 49 | 2.4 | 1.4 | 60 | 60 | 51 | 1.00 | 0.85 |

TABLE 6-continued

Longitudinal CD3 and CD2 antigen density (median fluorescence intensity and index) in response to intramammary *S. aureus* inoculation.

| Time/Cow | Blood MFI | | | Blood ADI | | Milk MFI* | | | Milk ADI* | |
|---|---|---|---|---|---|---|---|---|---|---|
| | Ctl | CD3 | CD2 | CD3 | CD2 | Ctl | CD3 | CD2 | CD 3 | CD2 |
| 1 dpi | | | | | | | | | | |
| A | 23 | 316 | 177 | 13.7 | 7.7 | 71 | 186 | 164 | 2.62 | 2.31 |
| B | 17 | 105 | 65 | 6.2 | 3.8 | 11 | 50 | 59 | 4.54 | 5.36 |
| C | 17 | 87 | 51 | 5.1 | 3.0 | 24 | 48 | 51 | 2.00 | 2.12 |
| D | 18 | 104 | 53 | 5.8 | 2.9 | 32 | 74 | 64 | 2.31 | 2.00 |
| E | 25 | 110 | 44 | 4.4 | 1.8 | 28 | 70 | 73 | 2.50 | 2.67 |
| F | 70 | 267 | 151 | 3.8 | 2.2 | 35 | 121 | 129 | 3.46 | 3.68 |
| 4–8 dpi | | | | | | | | | | |
| A | 26 | 274 | 168 | 10.5 | 6.5 | 37 | 85 | 119 | 2.30 | 3.22 |
| B | 14 | 76 | 51 | 5.4 | 3.6 | 20 | 39 | 55 | 1.95 | 2.75 |
| C | 40 | 94 | 51 | 2.3 | 1.3 | 23 | 37 | 46 | 1.61 | 2.00 |
| D | 20 | 123 | 51 | 6.1 | 2.6 | 35 | 83 | 62 | 2.37 | 1.77 |
| E | 25 | 96 | 43 | 3.8 | 1.7 | 27 | 58 | 51 | 2.15 | 1.88 |
| F | 9 | 74 | 48 | 8.2 | 5.3 | 17 | 55 | 44 | 3.23 | 2.59 |
| 9–14 dpi | | | | | | | | | | |
| A | 13 | 108 | 57 | 8.3 | 4.4 | 20 | 54 | 58 | 2.70 | 2.90 |
| B | 15 | 24 | 56 | 1.6 | 3.7 | 17 | ND | 72 | ND | 4.23 |
| C | 64 | 100 | 53 | 1.6 | 0.8 | 32 | 58 | 33 | 1.81 | 1.03 |
| D | 71 | 92 | 47 | 1.3 | 0.7 | 35 | 75 | 70 | 2.14 | 2.00 |
| E | 19 | 106 | 50 | 5.6 | 2.6 | 11 | 53 | 43 | 4.81 | 3.91 |
| F | 16 | 85 | 48 | 5.3 | 3.0 | 18 | 58 | 46 | 3.22 | 2.55 |

Figure 3:
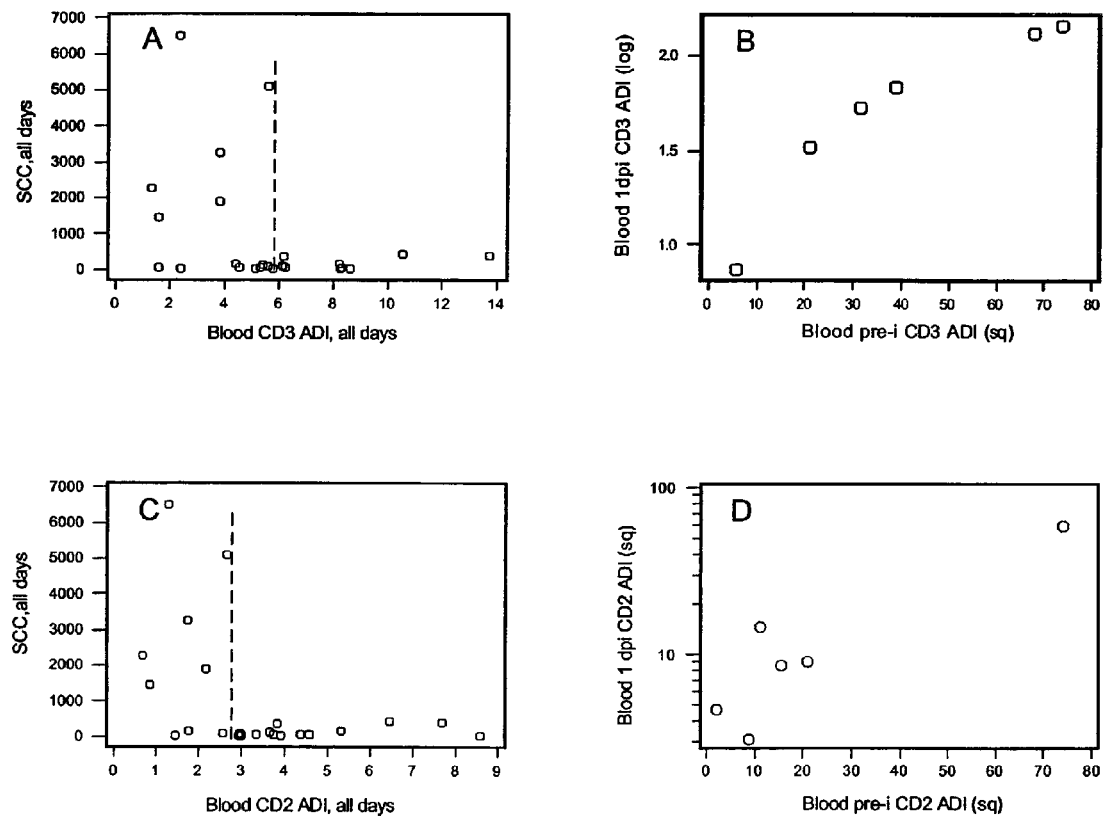
FIG. 3 shows the relationships between SCC vs. blood CD3 and CD2 antigen density. A: Scatterplot of CD3+ antigen density index per blood lymphocyte (ADI) versus somatic cell counts ($1\times10^3$ SCC/mL) (n=24 observations [all pre- and post-inoculation observations]). B: Correlation of pre-inoculation (pre-i) versus 1 day post-inoculation (1 dpi) blood CD3 antigen density index (ADI). Pre-i data are square root-transformed, 1 dpi data are log-transformed (n=6 cows). C: Scatterplot of CD2+ antigen density index per blood lymphocyte (ADI) versus somatic cell counts (SCC) (n=24 observations [all pre- and post-inoculation observations]). D: Correlation of pre-inoculation (pre-i) versus 1 day post-inoculation (dpi) blood CD2 antigen density index (ADI). Data are square root-transformed (n=6 cows).

*Values reported are composite means determined from both inoculated quarters
ADI - antigen density index (ADI is = MFI [CD2, CD3]/MIFI Ctl); A–F - individual animals; Ctl - control antibody; dpi - day(s) post-inoculation; MFI - Median fluorescence intensity; ND - not done; pre-i - pre-inoculation No cow with blood lymphocyte CD3 antigen density index (ADI)≧6 or blood lymphocyte CD2 ADI greater than 2.5 showed SCC≧500,000/mL (FIG. 3A, C). Vice versa, all mastitic cows displayed CD3 and CD2 ADI less than 6 or 2.5, respectively. Pre-challenge blood CD3 and CD2 antigen density values (those of non-mastitic cows) were predictive of 1 day post-challenge values (r≧0.93, P≦0.01, FIG. 3B, D).

The highest prediction of SCC by an individual indicator was found when SCC was regressed on blood CD2 antigen density (adjusted $R^{2=19.3}$%, P≦0.02). When the antigen density index of all of these markers on milk cells was analyzed against SCC, only CD3 ADI approached significance (P=0.06). However, the highest explanatory prediction of SCC was obtained when both blood CD2 ADI and milk CD3 ADI were analyzed ($R^2$= 41%, adjusted $R^2$=34.6%, P=0.006). This analysis indicated a positive relationship between CD3 and SCC and a negative relationship between CD2 and SCC(SCC, log-transformed, all days=5.90+[0.145 milk CD3 ADI, square-transformed, all days,]−[1.51 CD2 blood ADI, log-transformed, all days]).

EXAMPLE 3

Cell Activation/Cell Migration

This embodiment describes the expression of CD3 and CD11b antigens on leukocytes in milk after induced *S. aureus* mastitis. Mastitis was induced as described in Example 1. Milk collection, isolation of leukocytes was also carried out as described in Example 1. Cell types were identified on the basis of forward and side scatter. Backgating was conducted on CD3$^+$ (T lymphocytes) or CD3$^-$ cells (non-T lymphocytes) as described. Each sample was assessed by use of a 2-step procedure that included preliminary identification of cell populations by scatter light in terms of cell size (forward scatter) and granularity (side scatter) followed by analysis of the fluorescence gating on each cell population's preliminary bitmap. This procedure was repeated and the bitmap adjusted until the final bitmap corresponded to the lowest possible background fluorescence (ie, fluorescence of cells stained with the negative control antibody) and the highest possible specific fluorescence (i.e., fluorescence of cells stained with anti-CD3 or -CD 11b). At least 40,000 cells were acquired per test to obtain enough of the cell type least represented in each sample. Data were acquired and analyzed, using commercial software. The percentage of CD3$^+$ and CD11b$^+$ cells and the median fluorescence intensity (MFI) of each population were determined.

Data analysis—Cell-surface antigen density determined for a given sample was calculated as the MFI of CD3$^+$ or CD11b$^+$ cells divided by the MFI of cells stained with the negative control antibody. The net cell-surface antigen density 1 day after inoculation was calculated by dividing the MFI of CD3$^+$ or CD11b$^+$ cells determined on day 1 by the MFI of the respective population determined on day 0. Likewise, overall antigen density during the early phase of infection (days 1 to 8 after inoculation) was calculated by dividing the mean MFI determined during this period by the MFI determined on day 0.

Determination of sensitivity and specificity-Sensitivity and specificity of SCC, P/L index, and CD11b antigen density on milk macrophages as indicators of inflammation were determined. Sensitivity was defined as the ratio of true positive results (i.e., inflammation) to all positive results and specificity as the ratio of true negative results (i.e., no inflammation) to all negative results. Because there was no standard with which to compare bacteriologic culture results, bacteriologic results were regarded as 100% sensitive and 100% specific. For SCC, P/L index, and CD11b antigen density, true positive results were assumed to be those that yielded bacterial growth, and were greater than the upper limit of the 99% confidence interval (CI) determined prior to infusion (ie, on day 0; SCC, 70×10$^3$ cells/ml; P/L index, 1.55; CD11b antigen density, 1.81). True negative results were results of analyses of any sample from control cows or bacteria-negative samples from inoculated cows that were within the 99% CI determined on day 0. False-positive results were results of analyses of samples from any control cow that were greater than the upper limit of the 99% CI determined on day 0. Finally, false-negative results were results of analyses of bacteria-positive samples from inoculated cows that were within the 99% CI determined on day 0. Statistical analyses was carried out as described in Example 1.

Results

Figure 4:
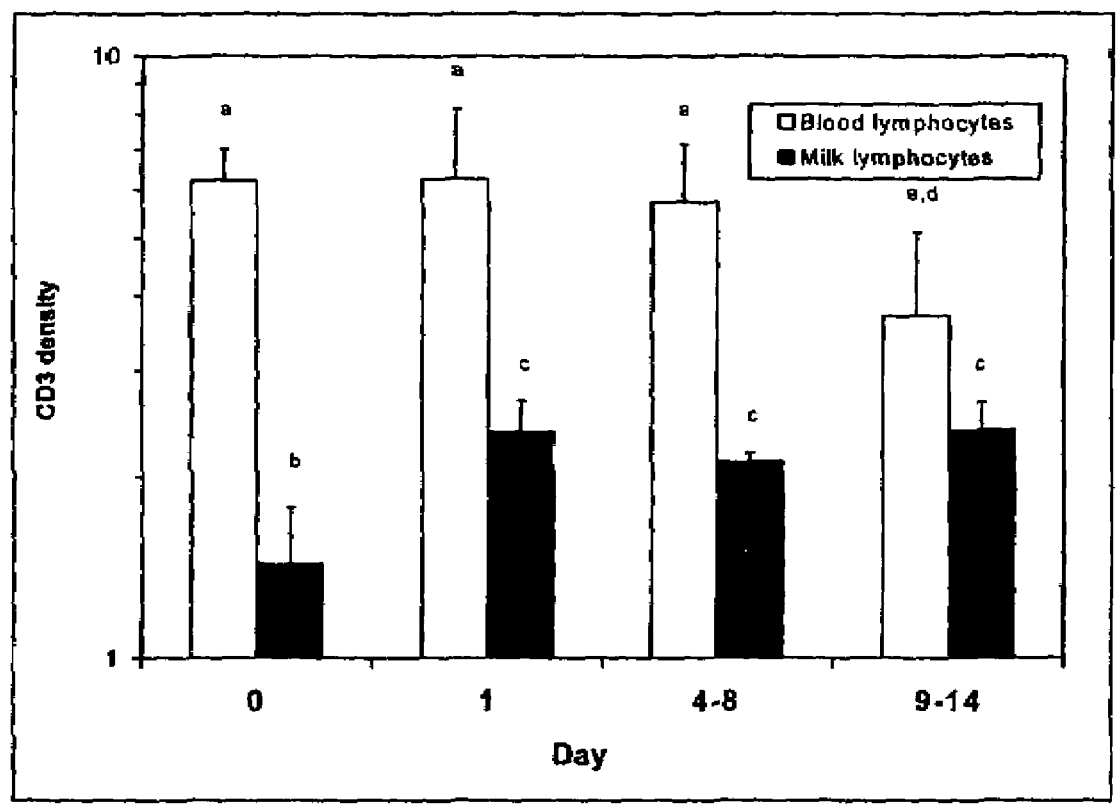
FIG. 4 shows the mean (±SD) density of CD3 antigen on blood and milk lymphocytes before (day 0) and after intramammary infusion of 200 CFU of S aureus into the left rear and right fore quarters of 6 first-lactation Holstein cows. Antigen density was determined by use of flow cytometry and was calculated as the ratio of the median fluorescence intensity (MFI) of antigen-positive cells divided by the MFI of cells stained with the negative control antibody. See FIG. 1 for key.
Figure 5:
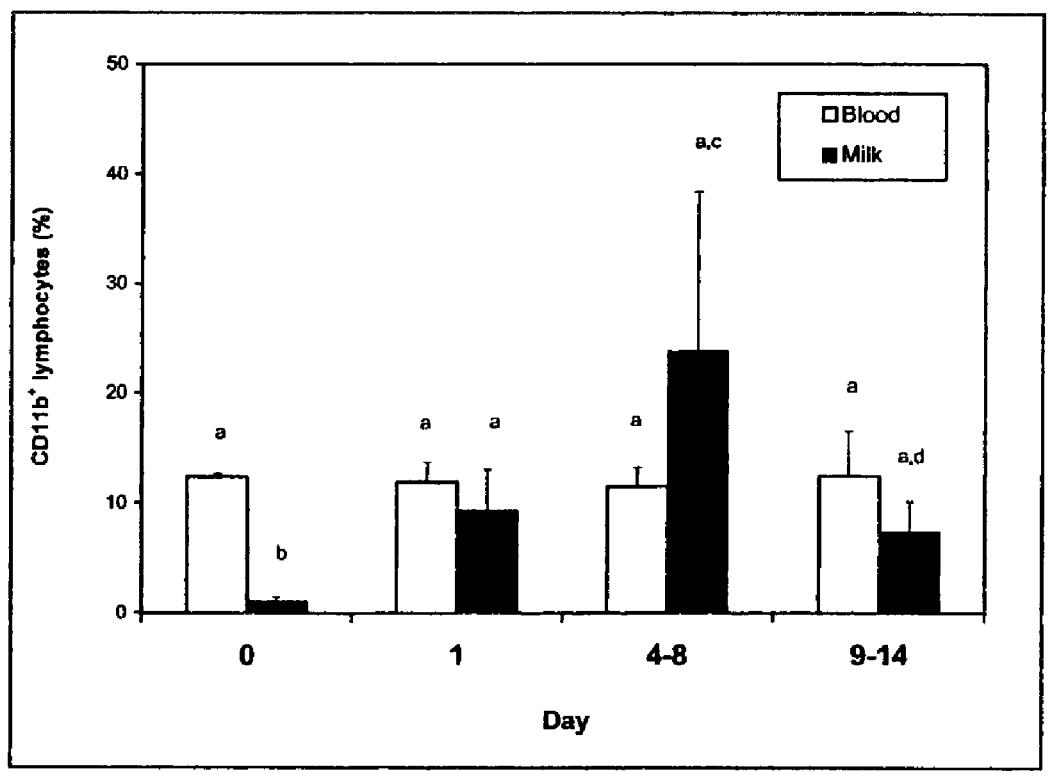
FIG. 5 shows the mean (±SD) percentage of CD11b$^+$ lymphocytes in blood and milk before (day 0) and after intramammary infusion of 200 CFU of S aureus into the left rear and right fore quarters of 6 first-lactation Holstein cows. See FIG. 1 for key.
Figure 6:
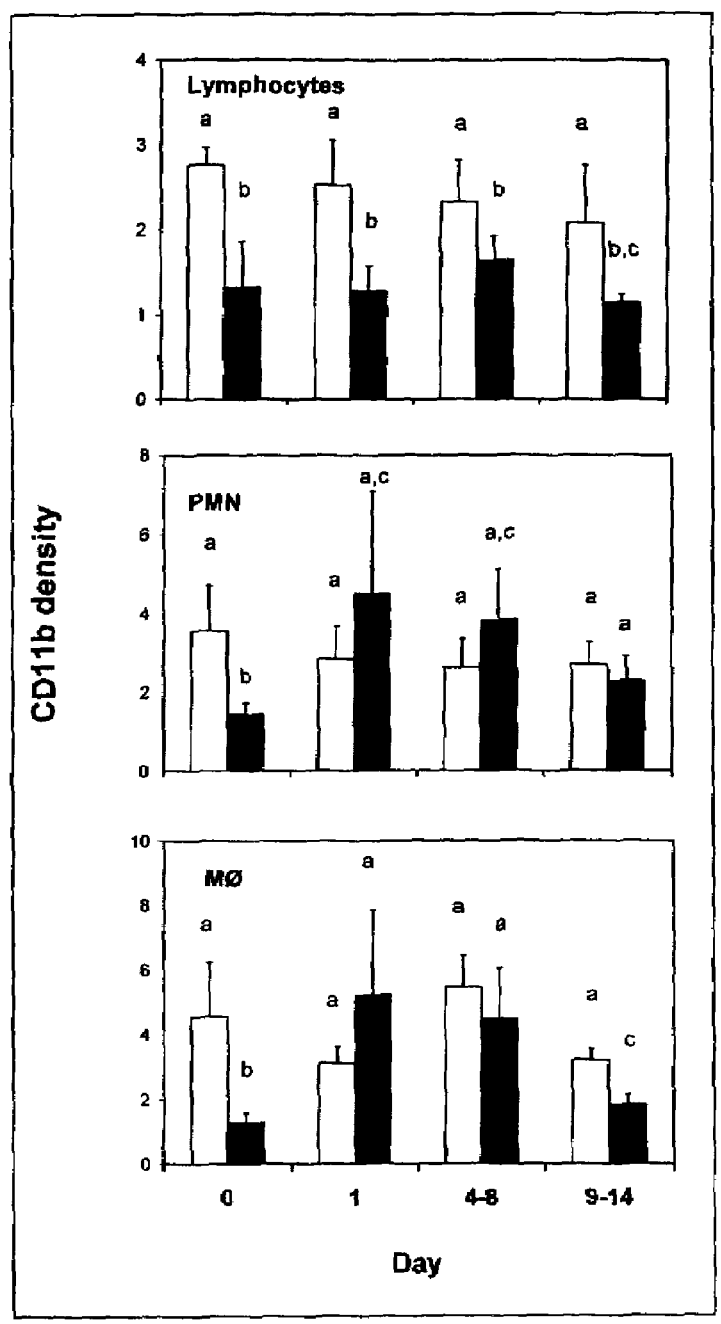
FIG. 6 shows the mean (±SD) density of CD11b antigen on leukocyte subsets in blood (open bar) and milk (closed bar) before (day 0) and after intramammary infusion of 200 CFU of S aureus into the left rear and right fore quarters of 6 first-lactation Holstein cows. See FIGS. 1 and 4 for key.

Leukocyte phenotypes in inoculated cows—The combined use of light scatter and fluorescence (backgating) allowed the identification of T lymphocytes (ie, CD3$^+$ cells) and distinguish PMN cells (CD11b$^+$ and high granularity [side scatter]) from macrophages (CD11b$^+$ and intermediate granularity; FIG. 1). A longitudinal analysis allowed the identification of the beginning, peak, and duration of CD3 and CD11b molecule up-regulation. Cell-surface CD3 density decreased on blood lymphocytes and increased on milk lymphocytes after intramammary infusion of $S$ $aureus$ (FIG. 4). In addition, percentage of CD11b$^+$ lymphocytes in milk significantly increased after inoculation as did lymphocyte antigen density; both values peaked on days 4 to 8 (FIGS. 5 and 6). There was a 2-fold increase in CD11b antigen density on milk PMN and at least a 3-fold increase on milk macrophages during the early inflammatory phase, compared with preinoculation values.

Figure 7:
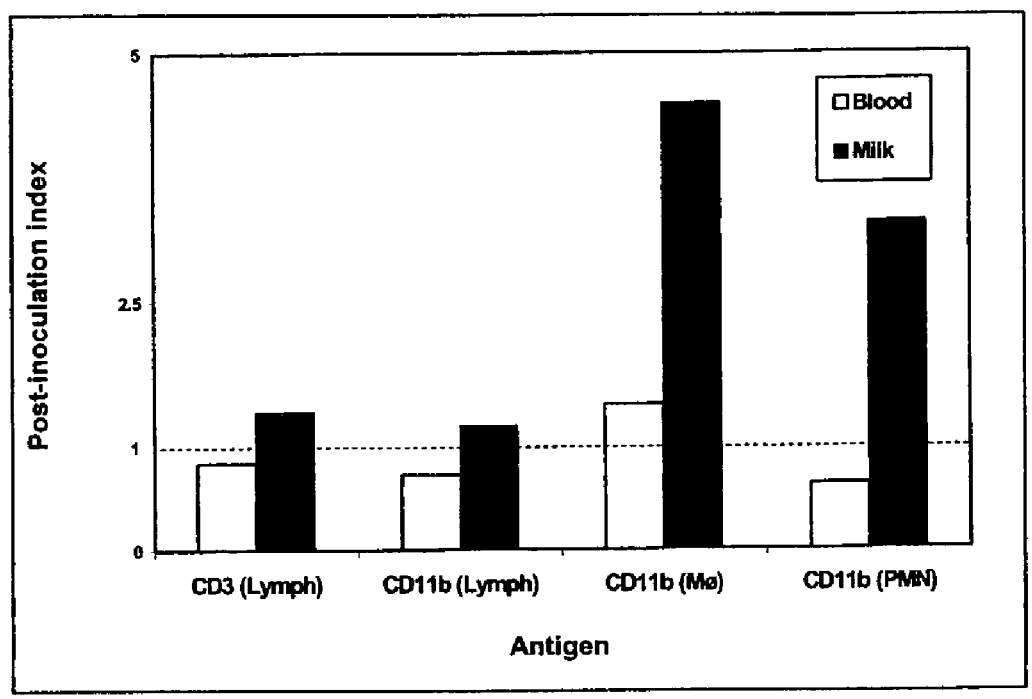
FIG. 7 shows the postinoculation CD11b and CD3 indices determined during the early inflammatory phase (1 to 8 days after intramammary infusion of bacteria) of S aureus-induced mastitis in 6 cows. Postinoculation indices were calculated by dividing the median antigen density determined throughout the early inflammatory phase by the median value determined prior to infusion (day-0 value). Indices for milk leukocytes were significantly ($P<0.05$) greater than indices for blood leukocytes. Lymph=Lymphocytes.
Figure 8:
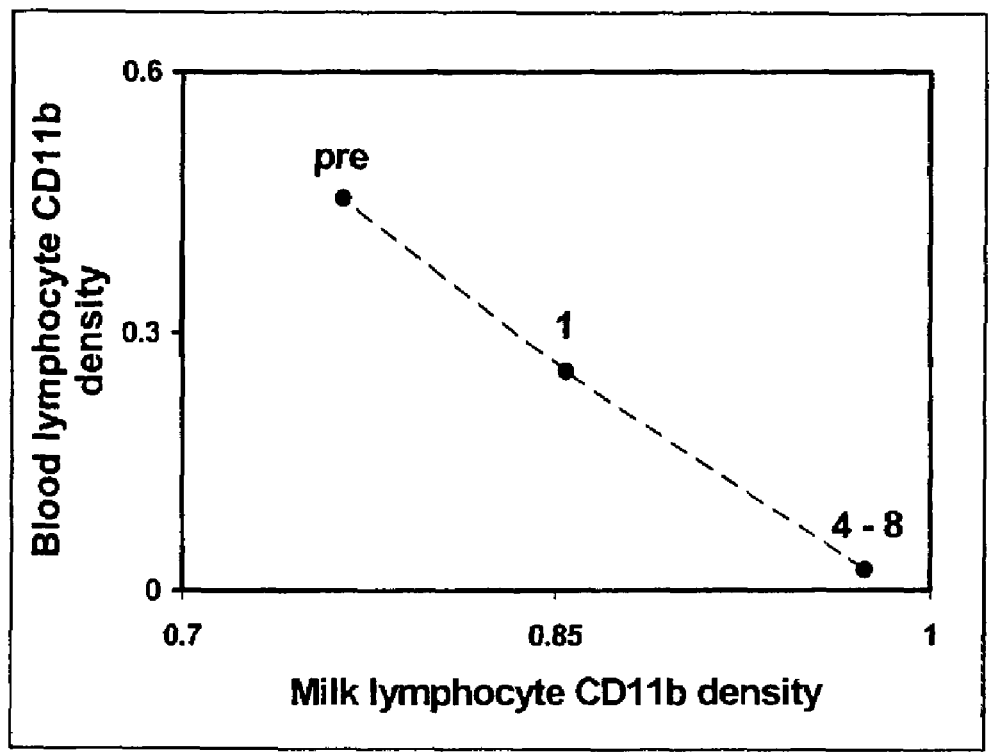
FIG. 8 shows a scatterplot of CD11b antigen density on lymphocytes in blood versus density on lymphocytes in milk before (pre) and 1 and 4 to 8 days after intramammary infusion of 200 CFU of S aureus into the left rear and right fore quarters of 6 first-lactation Holstein cows. Each point represents the median value. A significant negative correlation (r=−0.999, P=0.03) was detected.

Biomarkers of milk and blood leukocytes were compared during the early inflammatory phase of $S$ $aureus$-induced mastitis in order to assess whether changes in blood leukocyte phenotypes were related to those in milk. To do this, CD11b and CD3 postinoculation indices for each leukocyte type were calculated by dividing the median CD11b or CD3 density obtained on days 1 to 8 by the median value obtained on day 0. Milk lymphocyte CD3 and milk lymphocyte, macrophage, and PMN cell CD11b postinoculation indices were >1, indicating that antigen density on each cell type increased after inoculation. In contrast, blood lymphocyte CD3 and blood lymphocyte and PMN cell CD11b indices were <1, indicating that antigen density on these cells decreased after inoculation (FIG. 7). In addition, a significant negative correlation (r=−0.999 between CD11b density on blood lymphocytes and that on milk lymphocytes was detected over time (FIG. 8). In contrast, the blood monocyte CD11b postinoculation index was >1, indicating that antigen density increased on monocytes following intramammary infusion of $S$ $aureus$ (FIG. 7). However, when data for individual cows were analyzed, CD11b density on blood monocytes increased in only 3 of the 6 inoculated cows.

Relationships between leukocyte phenotypes, bacterial counts, and SCC—Density of CD11b molecules on milk lymphocytes was positively associated (r=0.44) with that on milk macrophages. When data obtained at all 3 times after inoculation (ie, day 1, days 4 to 8, days 9 to 14) were averaged, slight but not significant negative correlations were detected between CD11b antigen density on blood and milk lymphocytes (r= −0.80), macrophages (r=−0.82), and PMN cells (r=−0.39).

The mean P/L index during the early inflammatory phase was positively correlated (r=0.79) with the percentage of CD11b$^+$ milk lymphocytes. However, this correlation was not significant (P=0.06). In addition, significant associations were not detected between SCC and CD11b density on milk macrophages or PMN cells at any time after inoculation.

Figure 9:
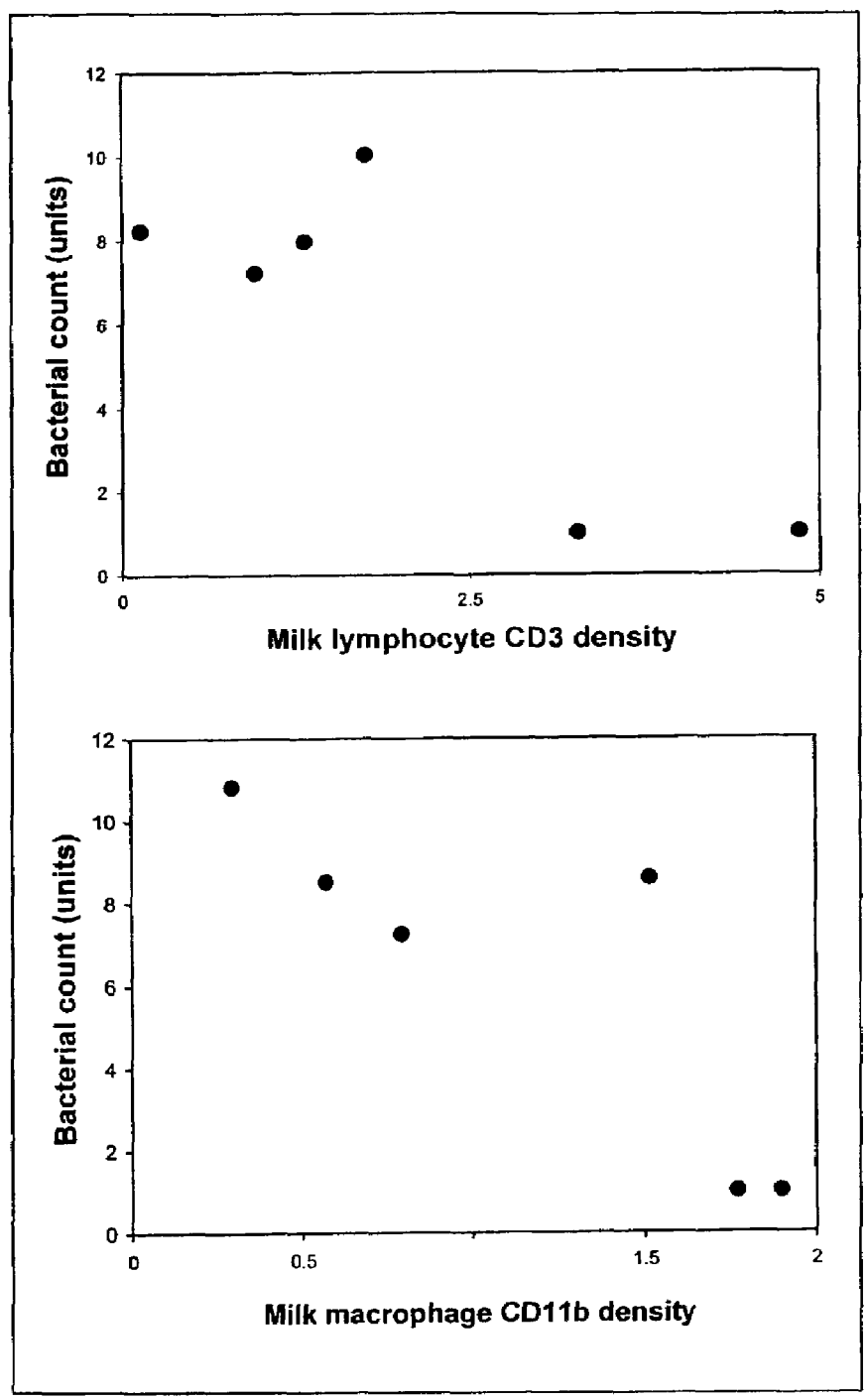
FIG. 9 shows a scatterplot of bacterial counts in milk samples versus CD3 antigen density on milk lymphocytes (top) or CD11b antigen density on milk macrophages (bottom). Antigen density was determined 1 day after intramammary infusion of 200 CFU of S aureus into the left rear and right fore quarters of 6 first-lactation Holstein cows; bacterial counts were determined on the same day (top) or between 9 and 14 days after infusion (bottom). Bacterial counts represent the mean of values determined for both infused quarters. Antigen density was negatively correlated with bacterial counts (CD3 density, r=−0.85, P<0.03; CD11b density, r=0.84, P= 0.04).

On day 1, mean CD11b density on milk PMN cells was negatively associated with bacterial counts. However, this association was not significant. In contrast, CD3 density on milk T lymphocytes was significantly associated (r=−0.85, P=0.03) with mean bacterial count on day 1, and CD11b density on milk macrophages on day 1 was significantly associated (r=−0.84, P=0.04) with bacterial count on days 9 to 14 (FIG. 9). Values expressed in FIG. 9 indicated (with 95% confidence) that milk lymphocyte CD3 ADI>2.5 and/or milk macrophage CD1 lb ADI>1.6 were associated with lack of bacterial growth. This means that the greater the antigen density (CD3, CD11b), the lower the bacterial ability to invade and growth (the greater the efficiency of the immune response).

No bacteria were recovered from milk samples from 2 of 6 inoculated cows (Table 7; cows A and B). However, the percentage of CD11b$^+$ milk phagocytes and the density of CD11b and CD3 molecules on milk phagocytes and lymphocytes, respectively, were significantly higher in these 2 cows, compared with the remaining 4 cows. On day 1, milk lymphocyte CD3 postinoculation indices for cows A and B were greater than the upper limit of the 99% confidence interval (CI) determined for the same index in the remaining cows. Similarly, milk macrophage and PMN cell CD11b indices for these 2 cows on day 1 was greater than the upper limit of the 91 and the 99% CI for each index, respectively, in the remaining cows.

TABLE 7

Milk leukocyte indices calculated from differential counts determined by use of cytologic methods and mastitis biomarkers (MB) before (day 0) and after intramammary infusion of 200 colony-forming units (CFU) of *Staphylococcus aureus* into the left rear and right fore quarters of 6 first-lactation Holstein cows

| Day | P/L index* | | P/M index† | |
| --- | --- | --- | --- | --- |
| | Cytology | MB | Cytology | MB |
| 0 | 0.49 | 0.388 | 0.44 | 0.630 |
| 1 | 2.57 | 8.410 | 2.51 | 4.440 |
| 4–8 | 1.65 | 6.360 | 1.67 | 3.170 |
| 9–14 | 1.35 | 3.950 | 1.23 | 1.532 |

*Cytologic and MB results were significantly correlated ($r = 0.97$; $P < 0.02$).
†Cytologic and MB results were significantly correlated ($r = 0.99$; $P < 0.02$).
P/L index = Ratio of percentage of phagocytes to percentage of lymphocytes. Pmn/M index = Ratio of percentage of polymorphonuclear (PMN) cells to percentage of macrophages.

Milk samples from 3 cows (C, E, and F) yielded the highest bacterial counts, and CD11b expression on milk lymphocytes peaked at a later time in these cows (after day 4), compared with cows A and B (day 1). These results suggest that time and CD antigen density, rather than antigen density alone, were associated with bacterial clearance.

On day 1, density of CD11b molecules on milk phagocytes was greater in cows A and B, compared with all other cows. At the same time, SCC in the infused quarters of these 2 cows were less than SCC in the remaining 4 cows (Table 7). Somatic cell counts also remained lower in cows A and B, compared with the other cows, at days 4 to 8 and 9 to 14.

The Pmn/M index in milk was significantly different among cows (Table 8). The lower limit of the 95% CI for the day-1 Pmn/M index determined for the 4 cows from which bacteria were recovered (3.46) was greater than that for cows A (3.20) and B (2.00). This suggests that the local (ie, mammary gland) immune response in cows from which bacteria were recovered was characterized by a greater number of PMN cells, compared with the response of cows from which no bacteria were recovered which was characterized by a greater number of macrophages. During the late inflammatory phase (day 9 to 14), Pmn/M indices for cows A and B were 0.06 and 0.01, respectively, indicating that macrophages predominated in these cows, whereas indices for the remaining cows were >0.76.

Differentiation between early and late inflammatory phases—The early inflammatory phase of *S aureus*-induced mastitis (days 1 to 8 after inoculation) was characterized by an increase in CD11b antigen density on milk leukocytes and an increase in the percentage of CD11b⁺ milk lymphocytes. Moreover, P/L and Pmn/M indices were significantly greater during the early phase, compared with the late phase (days 9 to 14 after inoculation; Table 9).

TABLE 8

Inflammatory responses induced by intramammary infusion of 200 CFU of *Staphylococcus aureus* in first-lactation Holstein cows

| Day* | Bacterial count (CFU/ml) | | SCC ($\times 10^3$/ml) | | P/L index† | P/M index† | CD11b ‡ |
| --- | --- | --- | --- | --- | --- | --- | --- |
| | LR | RF | LR | RF | | | |
| Cow A | | | | | | | |
| 0 | 0 | 0 | 21§ | 21§ | 0.25 | ND | 2.31 |
| 1 | 0 | 0 | 403§ | 403§ | 12.07 | 3.20 | 15.40 |
| 4–8 | 0 | 0 | 420§ | 420§ | 29.12 | 0.05 | 3.02 |
| 9–14 | 0 | 0 | 65§ | 65§ | 8.02 | 0.06 | 0.93 |
| Cow B | | | | | | | |
| 0 | 0 | 0 | 58 | 27 | 0.45 | ND | 0.90 |
| 1 | 0 | 0 | 713 | 27 | 1.31 | 2.00 | 5.28 |
| 4–8 | 0 | 0 | 193 | 78 | 11.65 | 3.80 | 3.75 |
| 9–14 | 0 | 0 | 70 | 41 | 0.26 | 0.01 | 2.76 |
| Cow C | | | | | | | |
| 0 | 0 | 0 | 47 | 47 | 0.23 | ND | 1.74 |
| 1 | 680 | 2,470 | 25 | 22 | 2.47 | 5.37 | 2.33 |
| 4–8 | 33,200 | 150 | 8,013 | 4,946 | 1.63 | 2.25 | 2.52 |
| 9–14 | 100,000 | 860 | 1,803 | 1,103 | 0.95 | 0.96 | 1.85 |
| Cow D | | | | | | | |
| 0 | 0 | 0 | 12 | 18 | 0.59 | ND | 1.10 |
| 1 | 0 | 3 | 12 | 61 | 6.47 | 6.71 | 2.33 |
| 4–8 | 4,840 | 530 | 80 | 101 | 3.30 | 4.54 | 1.90 |
| 9–14 | 2,320 | 490 | 1,626 | 2,909 | 3.42 | 0.79 | 1.99 |
| Cow E | | | | | | | |
| 0 | 0 | 0 | 66 | 122 | 0.30 | ND | 1.07 |
| 1 | 120 | 210 | 343 | 5 | 20.98 | 8.56 | 4.87 |
| 4–8 | 3,740 | 2,530 | 5,226 | 1,306 | 18.64 | 8.56 | 10.40 |
| 9–14 | 870 | 10,000 | 7,547 | 2,661 | 9.31 | 5.09 | 1.99 |
| Cow F | | | | | | | |
| 0 | 0 | 0 | 118 | 25 | 0.33 | ND | 0.65 |
| 1 | 120 | 0 | 1,407 | 463 | 8.93 | 4.48 | 1.15 |
| 4–8 | 10,000 | 2,720 | 11,500 | 71 | 34.81 | 4.08 | 5.37 |
| 9–14 | 10,000 | 0 | 10,000 | 10 | 2.92 | 0.99 | 1.51 |

*Milk samples were collected prior to infusion on day 0, 1 day after infusion (day 1), and once each between 4 and 8 days and 9 and 14 days after infusion.
†Determined by use of flow cytometry.
‡ Density of CD11b molecules on the surface of milk macrophages, determined by use of flow cytometry and calculated as the ratio of the median fluorescence intensity (MFI) of CD11b⁺ cells to the MFI of cells stained with the isotype control antibody.
§Values reported are means determined for both quarters.
SCC = Somatic cell count.
ND = Not determined.

TABLE 9

Phenotypic properties of milk leukocytes elicited during the early (1 to 8 days) and late (9 to 14 days) inflammatory phases of *S aureus*-induced mastitis in cows

| | Inflammatory phase | | |
| --- | --- | --- | --- |
| Property | Pre (n = 10) | Early (n = 6) | Late (n = 6) |
| Macrophage CD11b density | 0.79 to 1.80 | 2.45 to 7.26 | 1.34 to 2.34 |

TABLE 9-continued

Phenotypic properties of milk leukocytes elicited during the early (1 to 8 days) and late (9 to 14 days) inflammatory phases of S aureus-induced mastitis in cows

| | | Inflammatory phase | |
|---|---|---|---|
| Property | Pre (n = 10) | Early (n = 6) | Late (n = 6) |
| P/L index | 0.24 to 0.47 | 5.15 to 20.07 | 1.10 to 7.20 |
| Pmn/M index | ND | 2.79 to 6.14 | 0.00 to 2.64 |

The density of CD11b molecules on milk macrophages alone allowed us to distinguish between the early and late inflammatory phases. However, because bacteria were not recovered and SCC did not increase on day 1 in 6 of the 12 quarters inoculated with S aureus, SCC and bacterial recovery were not reliable markers of the early inflammatory phase.

Sensitivity and specificity—Sensitivity and specificity of SCC, P/L index, and CD11b antigen density on milk macrophages as indicators of inflammation were determined. Results indicated that sensitivity and specificity of flow cytometric indicators (ie, P/L index and CD11b density) were similar to or greater than those of SCC. Sensitivity and specificity of SCC were 87.5 and 83.3%, respectively, whereas values for P/L index were 93.7 and 91.7%, respectively, and for CD11b antigen density, 93.7 and 83.3%, respectively.

From these data, a relationship for the presence of absence of mastitis and for the stage of mastitis can be obtained. Thus, milk lymphocyte CD3 ADI is greater than 2.5 or a milk macrophage CD11b ADI greater than 1.6 is an indication of no bacterial counts (at >95% C.I.). Further, a milk macrophage CD11b ADI: greater than 1.33 is an indication of no mastitis (at >90% C.I.), greater than 2.45 is an indication of early mastitis (at >90% C.I.), greater than 1.34 but less than 2.45 is an indication of late mastitis (>90% C.I.).

EXAMPLE 4

Phagocytosis

Following isolation of leukocytes as described in Example 1, milk leukocyte differential counts (manual cytology) were determined at the Clinical Pathology Laboratory at Cornell University. Cells cultured with fluorescent microspheres were assessed with a fluorescent photomicroscope (model AX 70, Olympus, Melville, N.Y., USA) equipped with a digital camera (Kodak CDS 470, Rochester, N.Y., USA).

Macrophage and PMN cell counts were based on their forward and side scatter parameters and backgating (two-step procedure that optimizes preliminary gating according to fluorescence profiles) on CD3−, CD11b+ cells (phagocytes) as previously described. The phagocytosis assay was conducted with approximately five million leukocytes which were diluted into wash buffer (composed of 2% rabbit serum diluted in pH 7.2 PAE buffer [PBS with 0.1% $NaN_3$, 10% citrate, 10 mM EDTA]) and centrifuged for 10 minutes at 350 g. One million cells (100 $\mu$L) were transferred to each of four 12×75 mm polypropylene tubes, to which control antibody (tube I), CD3 (tube II), CD11b (tube III), or $5\times10^6$ FITC-conjugated latex microspheres (2.0 micron Fluoresbrite plain YG, catalog no. 18338-5, Polysciences, Inc. Warrington, Pa.) (tube IV) were added. FITC-labeled microspheres only (100 $\mu$L) were added to an additional tube (tube V). Cells were transferred to each of the first four tubes and resuspended into 50 $\mu$L of 10% rabbit serum in PAE. After 10 minutes on ice, 50 $\mu$L of isotype control, CD3 or CD11b antibody were added to each of the first three tubes and incubated for 30 minutes on ice. Fluorescent microspheres were either mixed with leukocytes in a 1:50 cell/microsphere ratio (tube IV) or left alone (tube V) and incubated 30 minutes at 38° C. with intermittent mixing. Cells were then washed three times with cold wash buffer and incubated with 100 $\mu$L of the secondary antibody (optimal dilution, FITC-conjugated rabbit anti mouse IgG [H&L chains] in 10% rabbit serum in PAE) (first three tubes only). After secondary antibody incubation for 30 minutes at 38° C. (first three tubes) or antibody-free incubation at 38° C. (tubes III and IV), all preparations were cooled down at 4° C., washed four times with wash buffer, fixed in 500 $\mu$L of 2% formaldehyde PBS-sodium azide, and kept at 4° C. until analyzed by flow cytometry (FACSCalibur, Becton-Dickinson, San Jose, Calif., USA). Cells were isolated, labeled and fixed within twelve hours of being collected. At least 40,000 cells were acquired per test. Data were analyzed with CELLQuest©software (Becton-Dickinson). The data here reported are those of 30-minute incubations.

Results

Figure 10:
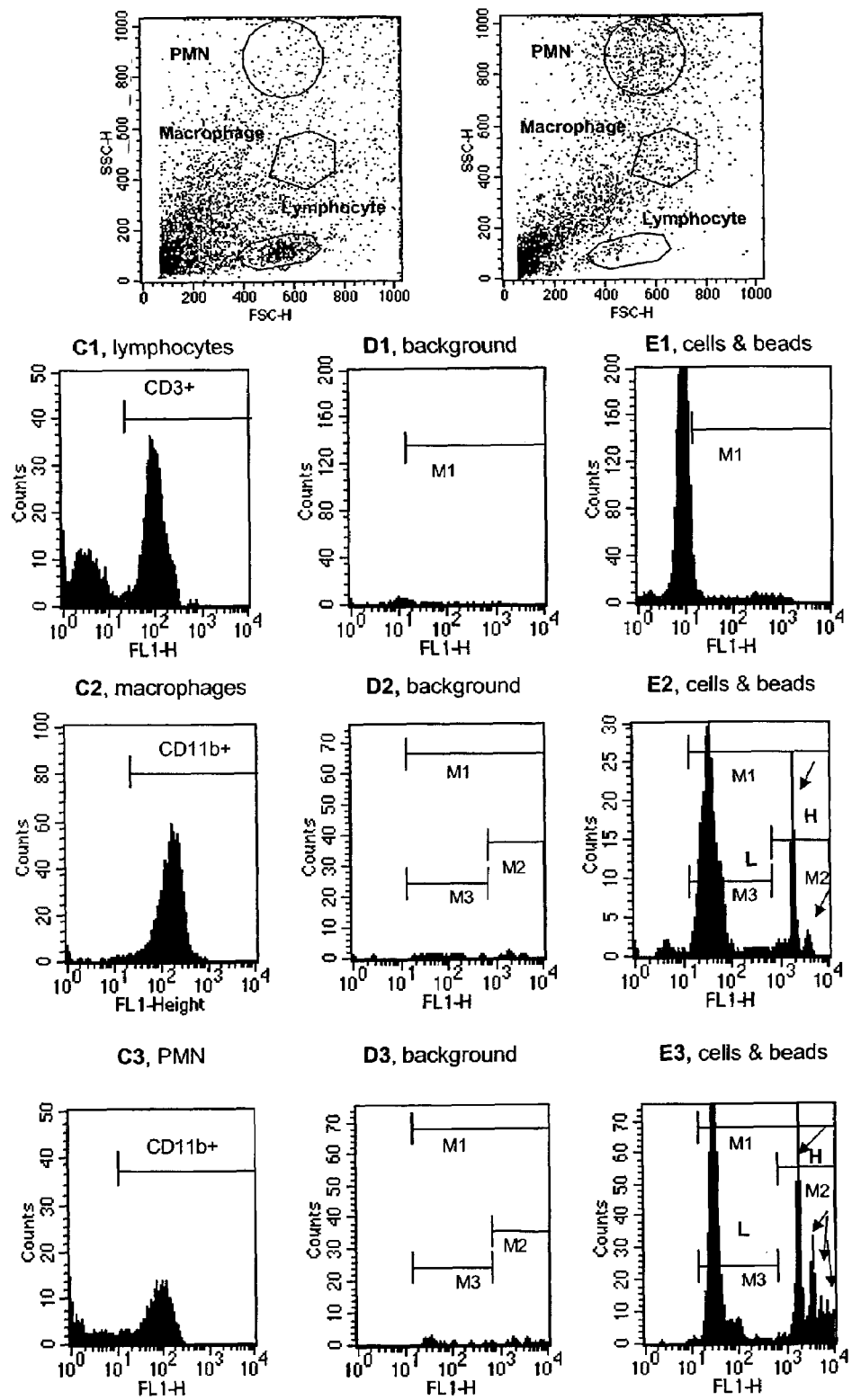
FIG. 10 shows flow cytometric assessment of phagocytosis. quantification of milk leukocytes. A, B: representative light scatter profile of lymphocytes, macrophages and PMN (light is reflected as a function of cell size [forward scatter or FSC-H] and cell granularity [side scatter or SCC-H] in non-mastitic (A) and mastitic (B) cows. $C_1$: representative CD3+ fluorescence (FL1-H) of lymphocyte bitmap (horizontal line represents the range of measured fluorescence above non-specific [background] fluorescence). C2, C3: representative CD11b+fluorescence of macrophage (C2), and PMN (C3) bitmaps. D1–D3: representative fluorescence profile of beads not exposed to leukocytes (lymphocyte [D1], macrophage [D2], and PMN [D3] bitmaps). E1–E3: representative fluorescence profile of beads exposed to leukocytes (lymphocyte [E1], macrophage [E2], and PMN [E3] bitmaps). E1–E3 histograms show the same fluorescence threshold for all leukocyte bitmaps: "M1" is set above the fluorescence profile observed within the lymphocyte subset (less than 5% background fluorescence). At least 98% of the events (cells cultured with fluorescent beads) observed in E2 and E3 are within "M1" (the range of fluorescence above that of the lymphocyte bitmap). Two distinct cell subpopulations are identified by fluorescent beads: a low fluorescence intensity (LFI or "L") sub-population (under "M3"), and a high fluorescence intensity (HFI or "H") sub-population (under "M2"), both in the macrophage (E2) and in the PMN (E3) bitmaps. The HFI sub-population shows several sub-sets (i.e., 2 peaks in macrophages and 5 peaks in PMN under "M2", seen in E2 and E3 [arrows]). The HFI/LFI index (percentage of events gated in M2/M3) in these examples is: 12.5% (macrophages, E2) and 56.6% (PMN, E3). The percent of actively phagocytizing phagocytes is 12.5% (macrophages) and 56.5% (PMN). Using the same settings, only background fluorescence (but not distinct sub-populations) are observed in D1–D3.
Figure 11:
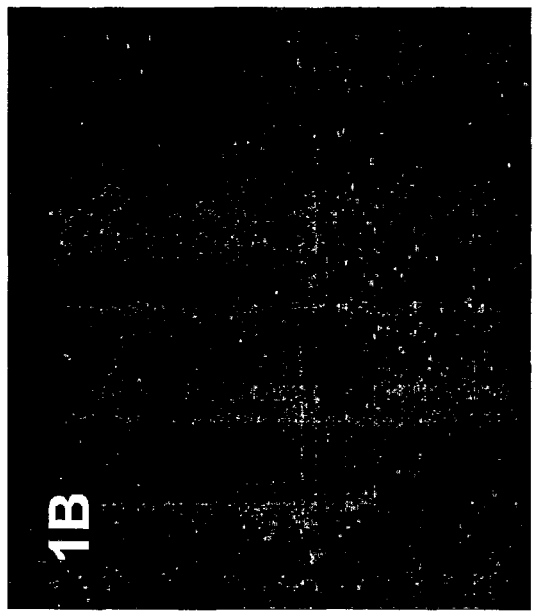
FIG. 11 shows phagocytosis of bovine mammary gland leukocytes. A: Bright field illumination (magnification: 40×). B: Fluorescent (ultraviolet) illumination (magnification: 40×). 1: Cell displaying high phagocytic activity. 2: Cell displaying low phagocytic activity. At least 3 (and probably 4) structures which fluoresce (1B) are observed inside the cytoplasm of an unstained phagocyte after incubation with fluorescent microspheres (i.e., phagocytized microspheres). In contrast, 2 fluorescent microspheres (and only partially) are attached to the cell (2B).
Figure 11:
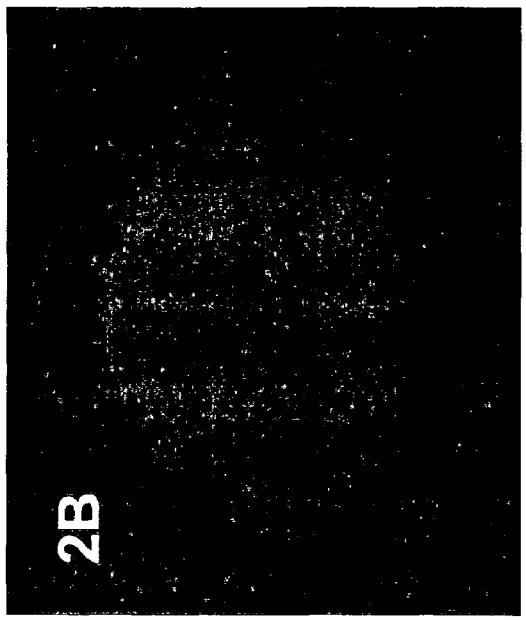
Figure 11:
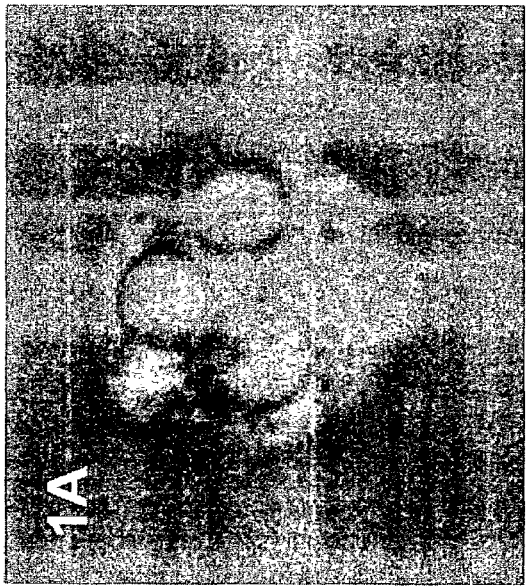
Figure 11:
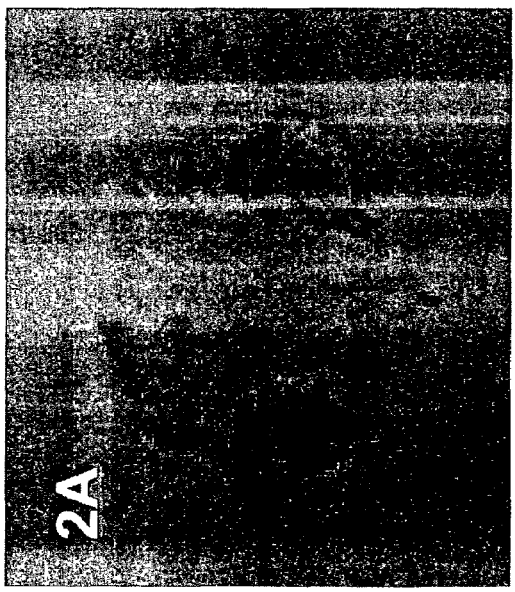

The fluorescence profile of phagocytes cultured with beads showed two major sub-populations of both macrophages and PMN, identified here as low fluorescence intensity (LFI) and high fluorescence intensity (HFI) sub-populations. Discontinuities in the fluorescence histogram allowed us to establish non-overlapping intervals of fluorescence intensity (M2, M3, FIG. 10). LFI cells appeared to be composed of two sub-subpopulations (lower/higher LFI). Additional (up to four) sub-subpopulations were observed within the HFI sub-population (M2, FIG. 11). Fluorescent microscopy indicated that most fluorescent beads had not been engulfed or were attached to the periphery of cells, while some cells had phagocytized up to four beads (FIG. 11).

Conventional cytology and flow cytometry-based cell all phagocyte counting (readings based on scatter light values) were positively correlated (r=0.83, P≦0.01). The scatter light-based phagocyte/lymphocyte index (P/L index) correlated positively with SCC (r=0.92, P≦0.01, Table 10B). However, flow cytometric assessments of phagocytes with fluorescent beads provided information not provided by cytology (both conventional and scatter light-based). Phagocytes differed significantly in their percentage of HFI cells: the 95% confidence interval for percentage of HFI cells was between 8.11 and 14.5 for macrophages; and for PMN, between 20.9 and 36.3 (P≦0.0001). A high/low median fluorescence intensity index (HFI/LFI), developed from the data, allowed us to differentiate PMN from macrophages: the HFI/LFI index was almost 3-fold greater for PMN (mean 0.47±0.13 [S.D.]) than for macrophages (mean 0.13±0.09 [S.D.], P≦0.001).

A significant negative relationship was observed between the overall percentage of PMN and the percentage of the HFI PMN sub-population (r=−0.72, P≦0.001). No significant relationship was found between macrophage percentage and the percentage of HFI macrophages. However, the percentage of HFI macrophages and HFI PMN was significantly and negatively correlated with mastitis (as expressed by the P/L index) both when assessed by individual correlation analysis (Table 10B) and together, when assessed by multivariate regression analysis (P/L index=4.67−[0.779 HFI Mø%]−[0.841 HFI PMN %], $R^2$=67%, P≦0.0001). Since the P/L index reflects the magnitude of the inflammatory response (the greater the phagocyte/lymphocyte ratio, the greater the mastitis), increases in the P/L index were mainly explained by variations in the opposite direction by HFI phagocytes (i.e., the greater the ability to phagocyte beads, the less chance of being mastitic).

Figure 12:
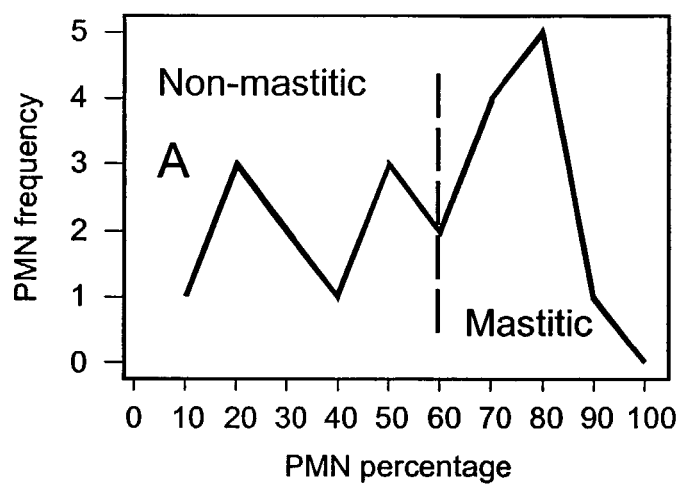
FIG. 12 is a representation of the analysis of conventional cytology and flow cytometry-based phagocytosis data. A: Distribution (histogram) of PMN percentage values. B: Distribution (histogram) of phagocytes (macrophages and PMN) percentage values. Vertical (broken) lines (A, B) represent the cut-off point between non-mastitic (left) and mastitic (right) observations. C: Distribution (boxplot) of high fluorescence intensity (HFI)/low fluorescence intensity (LFI) data. The horizontal line of each boxplot represents the median. Vertical (lower and upper) lines represent the 5% and 95% percentiles, respectively.
Figure 12:
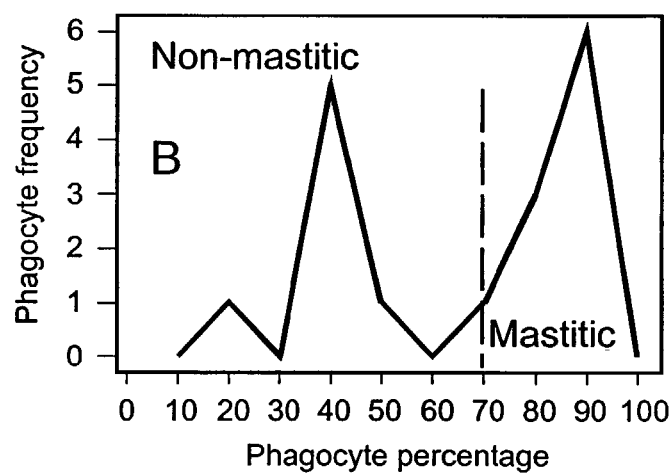
Figure 12:
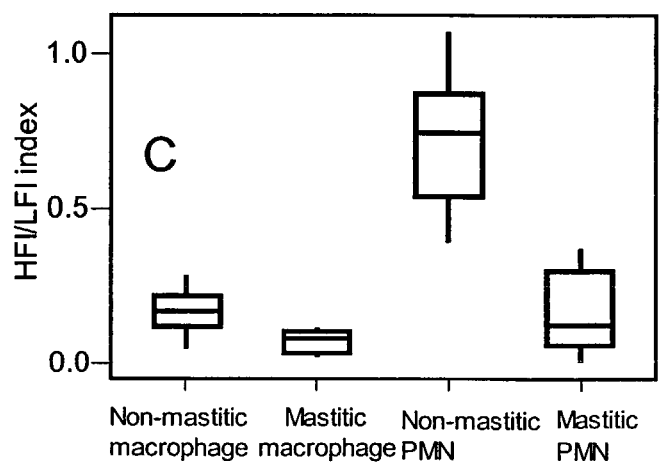

Statistical analysis of cytologic data was used to determine the cut-off points that differentiated non-mastitic from mastitic cows. Bimodal distribution of the data on percentages of PMN and percentages of all phagocytes (PMN and macrophages) suggested two distinct clusters of observations (FIG. 12A, B). Non-mastitic (or mastitic) observations were regarded to be those observed in the cluster of lower (or higher) phagocyte percentages, respectively. For the PMN percent (with 98% confidence) the upper limit of non-mastitic animals was 60.1%, and the lower limit of mastitic cows was 65.4%. For the overall phagocyte percent (99.6% confidence) the upper limit of non-mastitic cows was 72.3%, and the lower limit of mastitic cows was 80.7%. Since the percentage of all phagocytes provided greater confidence for achieving non-overlapping intervals, this indicator was adopted as the standard that identified individual observations as non-mastitic ($\leq 72.3\%$) or non-mastitic ($\geq 80.7\%$). Accordingly, there were 11 observations regarded to reflect non-mastitic and 9 observations estimated to correspond to mastitic animals (Table 10A).

Non-mastitic cows showed >11.04% of HFI macrophages and >34.30% of HFI PMN, while mastitic cows showed values below those thresholds (95% confidence interval). Mastitic cows showed a 2-fold smaller median macrophage HFI/LFI index and a 5-fold smaller median PMN HFI/LFI index than mastitic cows ($P \leq 0.03$, FIG. 12C).

Sensitivity and specificity of all of these indicators were assessed. Of the 5 variables evaluated (SCC, P/L, phagocyte percentage, PMN percentage and HFI PMN percentage), only the percentage of HFI PMN showed 100% sensitivity and specificity (Table 11). SCC showed the lowest values both in sensitivity and specificity. The P/L index was similar in sensitivity and specificity to the cytologic counterpart. This means that the variable of interest (non-mastitis/mastitis) was more accurately measured by the HFI PMN %. Therefore, the indicator that assessed cell function (HFI PMN %) was more sensitive and specific than any of the indicators that assessed morphology only.

TABLE 10

Bovine milk somatic cell counts, leukocyte counts, flow cytometric functional assessment of phagocyte sub-populations, and correlations between indicators.

A. Individual indicators

| | | cytology | | | light scatter | | | | fluorescent beads | | | | | |
| | | | | | | | | HFI | LFI | HFI | LFI | | |
| Cow/day[a] | SCC[b] | Pmn % | Mø % | Pha % | Pmn % | Mø % | Pha % | P/L | Pmn % | Pmn % | Mø % | Mø % | Pmn MFI | Mø MFI |
|---|---|---|---|---|---|---|---|---|---|---|---|---|---|---|
| 57-A# | 17 | * | * | * | 18.4 | 6.0 | 24.4 | 0.3 | 35.1 | 64.9 | 30.4 | 69.6 | 12.1 | 17.9 |
| 57-B# | 35 | 50 | 5 | 55 | 22.3 | 10.0 | 32.3 | 0.5 | 27.9 | 72.1 | 12.4 | 87.6 | 29.9 | 33.9 |
| 57-C# | 24 | 20 | 5 | 25 | 5.1 | 16.7 | 21.8 | 0.3 | 47.4 | 52.6 | 14.7 | 85.3 | 203.5 | 35.0 |
| 84-A | 75 | 80 | 15 | 95 | 25.3 | 36.0 | 61.3 | 1.6 | 9.2 | 90.8 | 7.8 | 92.3 | 10.1 | 9.4 |
| 84-B | 5808 | * | * | * | 98.2 | 1.0 | 99.2 | 122.6 | 0.2 | 99.8 | 2.7 | 97.3 | 2.7 | 2.0 |
| 84-C# | 186 | 30 | 15 | 45 | 6.0 | 20.0 | 26.0 | 0.4 | 35.0 | 65.0 | 10.8 | 89.2 | 27.6 | 13.8 |
| 68-A# | 30 | 13 | 35 | 48 | 2.4 | 31.3 | 33.7 | 0.5 | 51.7 | 48.3 | 14.4 | 85.6 | 983.4 | 10.9 |
| 68-B# | 10 | 30 | 14 | 44 | 8.5 | 12.2 | 20.7 | 0.3 | 42.8 | 57.2 | 10.5 | 89.5 | 29.7 | 15.1 |
| 79-A# | 59 | 64 | 18 | 82 | 10.0 | 26.0 | 36.0 | 0.6 | 45.8 | 54.2 | 16.0 | 84.0 | 46.6 | 13.6 |
| 79-B# | 37 | 83 | 9 | 92 | 73.7 | 8.0 | 81.7 | 4.4 | 46.5 | 53.5 | 17.9 | 82.1 | 46.0 | 18.4 |
| 18-A | 189 | 95 | 2 | 97 | 69.2 | 28.5 | 97.7 | 52.5 | 2.9 | 97.2 | 1.6 | 98.4 | 4.3 | 4.8 |
| 18-B | 297 | 78 | 15 | 93 | 60.0 | 30.1 | 90.1 | 9.2 | 26.6 | 73.4 | 10.4 | 89.6 | 20.0 | 19.1 |
| 74-A | 53 | 64 | 13 | 77 | 6.2 | 67.1 | 73.3 | 3.2 | 27.0 | 73.0 | 3.3 | 96.7 | 7.4 | 12.2 |
| 74-B | 82 | 70 | 13 | 83 | 14.2 | 14.1 | 28.3 | 1.0 | 19.4 | 80.6 | 8.6 | 91.4 | 23.0 | 23.9 |
| 74-C# | * | * | * | * | 38.7 | 14.9 | 53.6 | 0.9 | 46.6 | 53.4 | 4.3 | 95.8 | 74.3 | 26.9 |
| 22-A# | 22 | 25 | 21 | 46 | 7.4 | 4.0 | 11.4 | 0.1 | 37.5 | 62.5 | 22.2 | 77.8 | 9.3 | 9.7 |
| 22-B | 110 | 62 | 22 | 84 | 36.0 | 11.5 | 47.5 | 0.9 | 10.9 | 89.0 | 7.4 | 92.6 | 12.0 | 15.6 |
| 50-A | 75 | 88 | 10 | 98 | 84.6 | 7.3 | 91.9 | 11.4 | 14.5 | 85.5 | 10.1 | 89.9 | 6.9 | 9.3 |
| 50-B | 47 | 88 | 9 | 97 | 87.0 | 6.0 | 93.0 | 12.4 | 8.5 | 91.5 | 8.6 | 91.4 | 13.6 | 16.5 |
| 50-C# | 27 | 25 | 20 | 45 | 6.0 | 27.0 | 33.0 | 0.5 | 37.1 | 62.9 | 12.4 | 87.6 | 27.6 | 13.9 |

B. Correlations between indicators

| Variables | Correlation coefficient (r) | P value |
|---|---|---|
| SCC vs. P/LI (flow cytology) | 0.92 | <0.01 |
| Phagocyte % (cytology) vs. phagocyte % (flow cytometry) | 0.83 | <0.01 |
| PMN % (cytolology) vs. HMFI PMN % (flow cytometry) | −0.72 | <0.01 |
| Mø % (cytology) vs. HMFI Mø % (flow cytometry) | 0.38 | >0.1 |
| P/L (log, flow cytometry) vs. HMFI PMN % (log, flow cytometry) | −0.79 | <0.01 |
| P/L (log, flow cytometry) vs. HMFI Mø % (log, flow cytometry) | −0.69 | <0.01 |

HFI Mø—high fluorescence intensity macrophage % (medians); HFI Pmn—HFI polymorphonuclear %; LMFI Mø—low median fluorescence intensity macrophage %; LFI Pmn—LFI PMN %; Mø%—macrophage %; Mø MFI—macrophage [median] fluorescence intensity; Pha—phagocyte; P/L—phagocyte/lymphocyte index [macrophage and PMN counts]/lymphocyte counts; Pmn %—polymorphonuclear cell %; Pmn MFI—PMN [median] fluorescence intensity; SCC—somatic cell counts; #—non-mastitic (<80% phagocytes); *—not tested

[a] Cow number, observation (A, B, C)

[b] Composite SCC ($10^3$ cells/mL) from two quarters of the mammary gland

TABLE 11

Sensitivity and specificity of SCC, phagocyte/lymphocyte index (P/L), and percentages of phagocytes, PMN, and PMN high median fluorescence intensity (HMFI).

|  | Positive | Negative | Total |
|---|---|---|---|
| SCC |  |  |  |
| True | 7 | 7 | 14 |
| False | 3 | 2 | 5 |
| Total | 10 | 9 | 19 |
| Sensitivity: 70% |  |  |  |
| Specificity: 77.8% |  |  |  |
| Phagocyte % (manual cytology) |  |  |  |
| True | 7 | 8 | 17 |
| False | 1 | 1 | 2 |
| Total | 8 | 9 | 19 |
| Sensitivity: 87.5% |  |  |  |
| Specificity: 88.9% |  |  |  |
| PMN % (manual cytology) |  |  |  |
| True | 8 | 7 | 15 |
| False | 0 | 2 | 2 |
| Total | 8 | 9 | 17 |
| Sensitivity: 100% |  |  |  |
| Specificity: 77.8% |  |  |  |
| P/L Index (scatter light) |  |  |  |
| True | 9 | 10 | 19 |
| False | 0 | 1 | 1 |
| Total | 9 | 11 | 20 |
| Sensitivity: 100% |  |  |  |
| Specificity: 90.1% |  |  |  |
| HMFI PMN % (phagocytosis assay) |  |  |  |
| True | 9 | 11 | 20 |
| False | 0 | 0 | 0 |
| Total | 9 | 11 | 20 |
| Sensitivity: 100% |  |  |  |
| Specificity: 100% |  |  |  |

REFERENCES

1. Piccinini R, Bronzo V, Moroni P, et al.: 1999, Study on the relationship between milk immune factors and *Staphylococus aureus* intramammary infections in dairy cows. J Dairy Res 66:501–510.
2. Le Roux Y, Colin O, Laurent F: 1995, Proteolysis of quarter milk with varying somatic cell counts. 1. Comparison of some indicators of endogenous proteolysis in milk. J Dairy Sci 78: 1289–1297.
3. Wilson D J, Das H H, González R N, Sears P M: 1997, Association between management practices, dairy herd characteristics, and somatic cell count of bulk tank milk. J Am Vet Med Assoc 210:1499–1502.
4. Schukken Y H, Mallard B A, Dekkers J C M, et al.: 1994, Genetic impact on the risk of intramammary infection following *Staphylococcus aureus* challenge. J Dairy Sci 77: 639–647.
5. Kitchen, B J: 1981, Review of the progress of dairy science: bovine mastitis, milk compositional changes and related diagnostic tests. J Dairy Sci 48: 167–188.
6. Redelman D, Butler S, Robinson J, Garner D: 1988, Identification of inflammatory cells in bovine milk by flow cytometry. Cytometry 9:463–468.
7. Rümke C L: 1979 The statistically expected variability in differential leukocyte counting. In: Differential leukocyte counting, ed. Koepke J A, pp. 39–45. College of American Pathologists, Skokie, Ill.
8. Yang T J, Ayoub I A, Rewinski M J: 1997, Lactation stage-dependent changes of lymphocyte subpopulations in mammary secretions: inversion of CD4+/CD8+ T cells ratios at parturition. Am J Rep Immunol 37:378–383.
9. Springer T A: 1995, Traffic signals on endothelium for lymphocyte recirculation and leukocyte emigration. Annu Rev Physiol 57: 827–872.
10. Rivas A L, González R N, Wiedmann M, et al.: 1997, Diversity of *Streptococcus agalactiae* and *Staphylococcus aureus* ribotypes recovered from New York dairy herds. Am J Vet Res 58:482–487.
11. Schmaltz R: 1996, Characterisation of leucocytic somatic cells in bovine milk. Res Vet Sci 61:179–181.
12. Webster G A, Bowles M J, Karim M S, et al.: 1995, Flow cytometric analysis of peripheral blood lymphocyte subset light scatter characteristics as a means of monitoring the development of rat small bowel allograft rejection. Clin Exp Immunol 100:536–542.

What is claimed is:

1. A method for identifying the presence or absence of mastitis and if present, the stage of mastitis in a lactating animal comprising the steps of
    obtaining a sample of milk or blood from the animal;
    isolating leukocytes from the sample of milk or blood;
    measuring phagocytic ability of phagocytes together with at least one indicator selected from the group consisting of: differential leukocyte counts, leukocyte cell surface antigen fluorescence for CD2, leukocyte cell surface antigen fluorescence for CD3, and leukocyte cell surface antigen fluorescence for CD11b,
    wherein the differential leukocyte count defines a relationship between cells selected from the group consisting of lymphocytes, macrophages and polymorphonuclear cells,
    wherein antigen fluorescence for CD2, CD3 and CD11b is obtained by binding of specific affinity molecules having fluorescent labels thereon,
    wherein a negative control comprising lymphocytes is used in determining the phagocytic ability of phagocytes; and
    comparing the measured indicators to predetermined ranges for said indicators for early stage mastitis, late stage mastitis and no mastitis, thereby identifying the absence of mastitis or the stage of mastitis in the animal at a confidence interval of greater than or equal to 90%.

2. The method of claim 1, wherein the indicator is differential leukocyte count measured as the ratio of lymphocytes to combined macrophages and polymorphonuclear cells.

3. The method of claim 1, wherein the indicator is differential leukocyte count measured as the ratio of polymorphonuclear cells to macrophages.

4. The method of claim 1, wherein the indicator is phagocytic ability of leukocytes measured as the ability of phagocytes to uptake fluorescent microspheres.

5. The method of claim 1, wherein the indicator is leukocyte cell surface antigen fluorescence for CD2, CD3 or CD11b.

6. The method of claim 1, wherein the differential leukocyte count is measured by flow cytometry.

7. The method of claim 1, wherein the animal is a bovine animal.

* * * * *